(12) United States Patent
Sooksimuang et al.

(10) Patent No.: US 11,578,040 B2
(45) Date of Patent: Feb. 14, 2023

(54) [5]HELICENE DERIVATIVES AS MOLECULAR REPORTERS FOR DIAGNOSTIC APPLICATIONS AND METHODS OF SYNTHESIS THEREFOR

(71) Applicant: NATIONAL SCIENCE AND TECHNOLOGY DEVELOPMENT AGENCY, PathumThani (TH)

(72) Inventors: Thanasat Sooksimuang, PathumThani (TH); Nitsara Karoonuthaisiri, PathumThani (TH); Ratthaphol Charlermroj, PathumThani (TH); Somboon Sahasithiwat, PathumThani (TH); Waraporn Panchan, PathumThani (TH); Manlika Makornwattana, PathumThani (TH); Sudtida Phuengwas, PathumThani (TH); Laongdao Kangkaew, PathumThani (TH)

(73) Assignee: National Science and Technology Development Agency, PathumThani (TH)

( * ) Notice: Subject to any disclaimer, the term of this patent is extended or adjusted under 35 U.S.C. 154(b) by 926 days.

(21) Appl. No.: 16/338,031

(22) PCT Filed: Sep. 29, 2017

(86) PCT No.: PCT/TH2017/000072
§ 371 (c)(1),
(2) Date: Mar. 29, 2019

(87) PCT Pub. No.: WO2018/063105
PCT Pub. Date: Apr. 5, 2018

(65) Prior Publication Data
US 2020/0017443 A1  Jan. 16, 2020

(30) Foreign Application Priority Data

Sep. 30, 2016 (TH) ............................. 1601005887
Sep. 30, 2016 (TH) ............................. 1601005888
(Continued)

(51) Int. Cl.
*G01N 21/76* (2006.01)
*C07D 209/58* (2006.01)
(Continued)

(52) U.S. Cl.
CPC .......... *C07D 209/58* (2013.01); *C07C 255/54* (2013.01); *C07C 309/11* (2013.01);
(Continued)

(58) Field of Classification Search
CPC ... C07D 209/58; C07C 255/54; C07C 309/11; C07C 2603/52; G01N 33/582; A61B 5/0071
See application file for complete search history.

(56) References Cited

PUBLICATIONS

Li et al. (Chem. Comm. 2014, 50, 2993-2995).*
PCT International Search Report and Written Opinion dated Jan. 4, 2018, issued in corresponding PCT International Application No. PCT/TH2017/000072 (8 pages).
Hisataka, Kobayashi et al., "New Strategies For Fluorescent Probe Design in Medical Diagnostic Imaging", Chemical Reviews, vol. 110, No. 5, May 12, 2010, pp. 2620-2640.
Sahasithiwat, S., et al., "3,12-Dimethoxy-7,8-dicyano-[5]helicene As A Novel Emissive Material For Organic Light-Emitting Diode", Synthetic Metals, Elsevier Sequoia, Lausanne, CH, vol. 160, No. 11-12, Jun. 1, 2010, pp. 1148-1152.

* cited by examiner

*Primary Examiner* — Michael G. Hartley
*Assistant Examiner* — Melissa J Perreira
(74) *Attorney, Agent, or Firm* — Finnegan, Henderson, Farabow, Garrett & Dunner, LLP

(57) ABSTRACT

The present invention provides the methods of synthesis of [5]helicene compounds and the use of the said compounds conjugating with biomolecules to work as molecular reporter for diagnostic. The compounds in the present invention have the chemical structure illustrated in the formula (1): wherein G is a connecting group composes of 2 carbon atoms selected from the group consisting of ethane and ethylene; A is a separated or connected group selected from the group consisting of cyano and imide; D1 is selected from the group consisting of oxyalkanoic acid, oxyalkanal and oxyalkanesulfonate; and D2 has structure selected from the group consisting of hydroxyl, oxyalkanoic acid, oxyalkanal, alkyl oxyalkanoate, oxyalkanol and oxyalkanesulfonate. The compounds in the present invention compose of aromatic [5]helicene core comprising long π-conjugating system. The said compounds contain functional groups which able to link with biomolecules and they are soluble in water or other solvents that used in binding process with biomolecules. Moreover, owing to having proper chemical structure, the compounds in the present invention exhibit good fluorescent emission in wavelength of 425-675 nm. When the said compounds connected with biomolecules, the biomolecules give good fluorescence and can be detected under ultraviolet radiation.

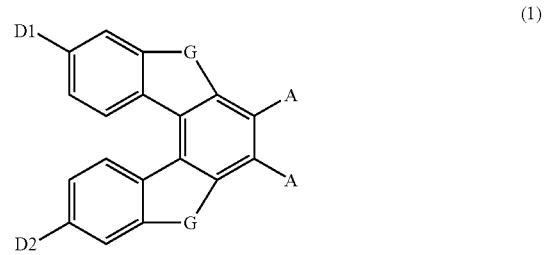

(1)

10 Claims, 5 Drawing Sheets

(30) Foreign Application Priority Data

| Sep. 30, 2016 | (TH) | 1601005889 |
| Sep. 30, 2016 | (TH) | 1601005890 |
| Sep. 22, 2017 | (TH) | 1701005538 |
| Sep. 25, 2017 | (TH) | 1701005608 |
| Sep. 25, 2017 | (TH) | 1701005612 |
| Sep. 25, 2017 | (TH) | 1701005613 |

(51) Int. Cl.
*C07C 255/54* (2006.01)
*C07C 309/11* (2006.01)
*G01N 33/58* (2006.01)
*A61B 5/00* (2006.01)

(52) U.S. Cl.
CPC .......... *G01N 33/582* (2013.01); *A61B 5/0071* (2013.01); *C07C 2603/52* (2017.05)

Test with mouse antibody labeling with molecular reporter compound 6

Test with carbonate buffer (A)

Test with mouse antibody labeling with molecular reporter compound 8

Test with carbonate buffer (B)

Test with mouse antibody labeling with molecular reporter compound 14

Test with carbonate buffer (C)

(A)

(B)

(C)

[5]HELICENE DERIVATIVES AS MOLECULAR REPORTERS FOR DIAGNOSTIC APPLICATIONS AND METHODS OF SYNTHESIS THEREFOR

CROSS-REFERENCE TO RELATED APPLICATIONS

This is a U.S. National Phase of PCT/TH2017/000072, filed Sep. 29, 2017, which claims the benefit of priority to Thailand Patent Application No. 1601005887, filed Sep. 30, 2016; Thailand Patent Application No. 1601005888, filed Sep. 30, 2016; Thailand Patent Application No. 1601005889, filed Sep. 30, 2016; Thailand Patent Application No. 1601005890, filed Sep. 30, 2016; Thailand Patent Application No. 1701005538, filed Sep. 22, 2017; Thailand Patent Application No. 1701005608, filed Sep. 25, 2017; Thailand Patent Application No. 1701005612, filed Sep. 25, 2017; and Thailand Patent Application No. 1701005613, filed Sep. 25, 2017 all of which are incorporated herein by reference.

FIELD OF THE INVENTION

The present invention relates to chemistry and more particularly to organic dyes based on derivatives of [5]helicene, the use as molecular reporters for diagnostic applications and methods of synthesis therefor.

SUMMARY OF THE INVENTION

The present invention provides organic dyes based on [5]helicene derivative compounds for conjugating with biomolecules and the use thereof as reporter molecules in diagnostic for microbials, toxins and toxicants in samples from agricultural industry, food and environment.

The structure of [5]helicene derivative compounds in the present invention are represented by the following chemical formula (1):

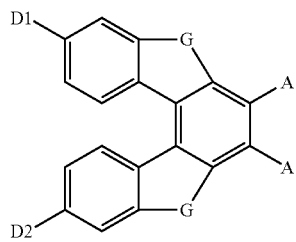
(1)

wherein

G is a connecting group composes of 2 carbon atoms selected from the group consisting of Ethane

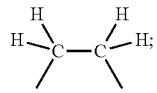

and

Ethylene

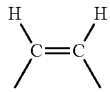

A is a separated or connected group selected from the group consisting of

Cyano

—CN; and

Imide

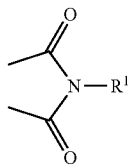

wherein R1 is selected from the group consisting of

Phenyl

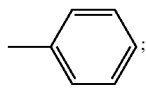

Alkyl

when a is a number of carbon atoms in aliphatic hydrocarbon and a equals to 1 to 7; and Alkanoic acid

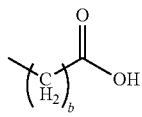

when b is a number of carbon atoms in aliphatic hydrocarbon and b equals to 1 to 7.

D1 is selected from the group consisting of

Oxyalkanoic acid

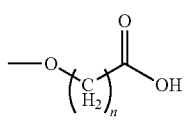

when n is a number of carbon atoms in aliphatic hydrocarbon and n equals to 1 to 7;

Oxyalkanal

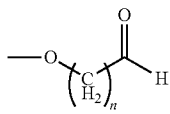

when n is a number of carbon atoms in aliphatic hydrocarbon and n equals to 1 to 7; and
Oxyalkanesulfonate

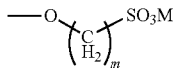

when M is a metal atom selected from the group consisting of sodium and potassium,
m is a number of carbon atoms in aliphatic hydrocarbon and m equals to 3 or 4.
D2 is selected from the group consisting of
Hydroxy
—OH;
Oxyalkanoic acid

when y is a number of carbon atoms in aliphatic hydrocarbon and y equals to 1 to 7;
Oxyalkanal

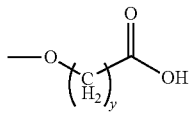

when y is a number of carbon atoms in aliphatic hydrocarbon and y equals to 1 to 7;
Alkyl oxyalkanoate

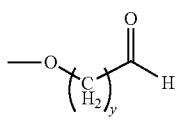

when y is a number of carbon atoms in aliphatic hydrocarbon and y equals to 1 to 7,
R2 is selected from the group consisting of methyl and ethyl group;
Oxyalkanol

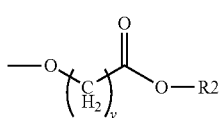

when z is a number of carbon atoms in aliphatic hydrocarbon and z equals to 2 to 8; and Oxyalkanesulfonate

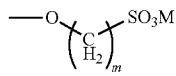

when M is a metal atom selected from the group consisting of sodium and potassium,
m is a number of carbon atoms in aliphatic hydrocarbon and m equals to 3 or 4.

The derivative of [5]helicene compounds in the present invention compose of aromatic [5]helicene core comprising long n-conjugating system. The said compounds contain functional groups which able to link with biomolecules and they are soluble in water or other solvents that used in binding process with biomolecules. Moreover, owing to having proper chemical structure, the compounds in the present invention exhibit good fluorescent emission in wavelength of 425-675 nm. When the said compounds connected with biomolecules, the biomolecules give good fluorescence and can be detected under ultraviolet radiation.

The other embodiment in this invention is the synthetic method of [5]helicene compounds comprising: step a) An O-alkylation reaction of the [5]helicene compound in formula (4), selected from the [5]helicene compound in formula (4) wherein A1 is imide or the [5]helicene compound in formula (4) wherein A1 is cyano, with haloalkanoic acid alkyl ester (I) in the present of base 1 in organic solvent 1 to give [5]helicene compound (5) and/or compound (6) as intermediate; step b) A hydrolysis reaction of [5]helicene compound (5) or compound (6) using base 2 in organic solvent 2 at temperature in the range of 25-150° C. for 1-24 hours, follow by acidify with acid 1 to gain pH 0 to obtain [5]helicene compound (7) or compound (8) as intermediate; step c) An O-alkylation reaction of the intermediate compound containing OH group, selected from of [5]helicene compound (4), compound (5) or compound (7), with alkane sultone (II) at the present of base 3 in an organic solvent 3 to obtain [5]helicene compound (9), compound (10) or compound (11) as final product of intermediate; and step d) A reduction reaction of intermediate containing ester group, selected from [5]helicene compound (5), compound (6) or compound (10), using diisobutylaluminum hydride, (DIBAL-H) in an organic solvent 4 to obtain [5]helicene compound (12), compound (13) and/or compound (14) and/or compound (15) or compound (16) as final product.

BACKGROUND OF THE INVENTION

Luminescent organic compounds are used as reporter molecules to give optical signal in biotechnology. The organic compounds are excited by a light source with a proper wavelength and give fluorescent light. The molecules can be attached to biomolecules, such as protein, antibody peptide or DNA, by covalent or non-covalent bonding specifically. When a luminescent organic compound is connected to a biomolecule, it can be commonly called a fluorophore. Mostly, reporter molecules comprise aromatic structure which make the molecules exhibit fluorescent emission.

There are many uses of luminescent materials for diagnostic in biotechnology especially for mycotoxin analysis. Mycotoxins are organic compounds produced by fungi and toxic to human and animal. The contamination of mycotoxin can be found in all food production chain in agriculture process, including prehavesting, posthavesting food processing, storage and logistic. Since many toxins are chemical resistance and highly thermal stability, they can be accumulated in human bodies and having an affect on health in short and long term, although fungi are killed.

Due to high toxicity of some mycotoxins, many food administators set the standard for the allowed amount of toxins in foods. For consumers safety, diagnostic for mycotoxins are very important for not only consumers but also food producers.

Mycotoxin diagnostic can be performed by immunochemical technique which composes of two main parts. An element that specifically binds with a target molecule is a selective recognition element. In case of the target molecule is mycotoxin, the recognition element can be antibody. The second element is reporter molecule which gives signal of the analysis. The example of commonly used reporter molecules include enzymes, radioactive compounds, nanoparticles, and fluorescent dyes or fluorophores. Due to different advantages of reporter molecules, objectives of analysis, methods of diagnostic and other considerations are needed to be taken into account for selecting a proper reporter molecule. For example, the fluorescent dyes or fluorophores give strong optical signal. Therefore, the analysis of a target molecule can be performed at very low concentration with high sensitivity. Nonetheless, the fluorescent compound can be prepared in large quantity with consistent properties in batch to batch synthesis.

One of the component in the development of diagnostic in biotechnology is reporter molecule. One of the key components of a diagnostic development in biotechnology is an effective reporter molecule. A fluorophore becomes a powerful reporter molecule for detection of multiple targets in many techniques such as in a multiplex real-time polymerase chain reaction and microarray technique. However, the usage of fluorophores is limited in the research only because an expensive detector is required to measure the fluorescent signal. Currently, fluorescent organic compounds are widely used as luminescent materials in many areas. Nevertheless, this type of fluorescent compounds was not suitable for linking to biorecognition element (e.g. antibody, peptide, and DNA) for diagnostic applications owing to their physiochemical properties: solubility and specific functional group for conjugation with the biorecognition element.

There are many fluorescent organic compounds or fluorophores widely used in biotechnology including fluorescein, rhodamine, BODIPY, squaraine and cyanine (Goncalves, Chem Rev 109(2009) 190-212; Kobayashi et al, Chem Rev 110(2010) 2620-2640; Gust, et al, Molecules 19(2014) 15824-15865) and their chemical structures are shown below.

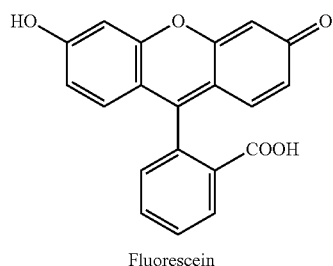

Fluorescein

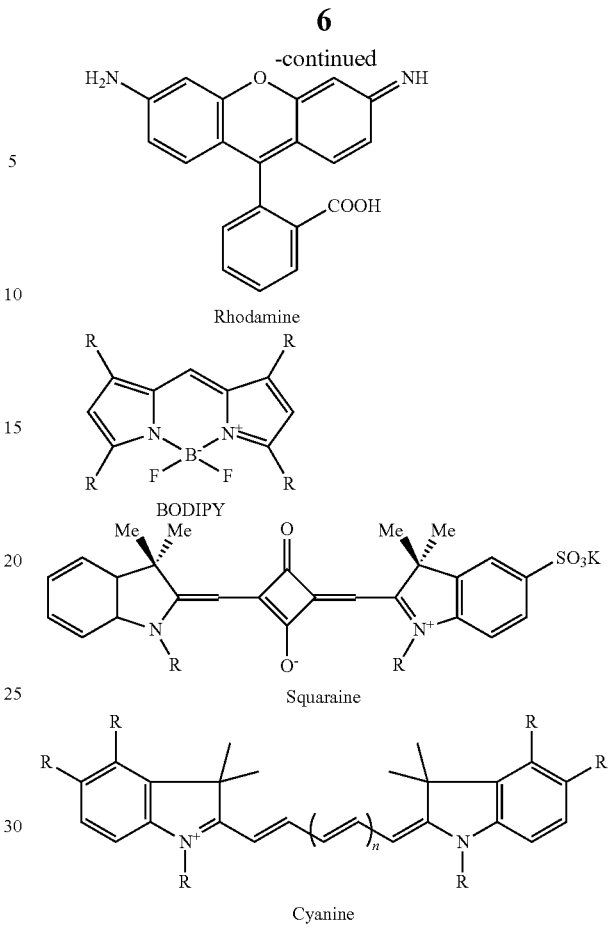

Fluorescent materials can be categorized in many ways such as emission wavelength or main chemical structure. Fluorescent compounds for diagnostic in biotechnology have been continuously developed to improve the desired properties for the application. The said characteristics include high molar extinction coefficient or molar absorptivity ($\varepsilon$), high fluorescence quantum efficiency ($\Phi_F$), high chemical stability, thermal stability and photo stability or optical stability. The compounds also should be soluble in solvents especially in water which used for conjugating the compounds with biomolecules. Importantly, after binding fluorescent compounds with biomolecules, the activity of the biomolecules should not decrease significantly.

The important development of luminescent organic compound for biotechnology is the synthesis of new organic compound. Some new compounds give better certain properties while decrease other performances. For instance, organic dye with long wavelength emission is generally a large molecule which less soluble than a small molecular dye. Moreover, when a large molecule conjugated with a biomolecule, it can possibly decreases the activity of the biomolecule. The optical properties such as absorption and emission are crucially taken into account for the development of luminescent organic dye. Many organic dyes, with small Stokes shift, absorb light in the visible region and emit light in the nearby excitation wavelength. However, an organic dye with a large Stokes shift is desired because the light from the diagnostic light source will not interfere the resulting emitted light from the reporter organic molecule. As a result, an organic dye with a large Stokes shift will provide a benefit to the design for a diagnostic test kit.

[5]Helicenes or pentahelicenes are hydrocarbon compounds compose of ortho-fused five aromatic rings resulting in helical out-of-plane structures. The unsubstituted derivatives give very low fluorescence quantum yields. The structure of [5]helicene is depicted below.

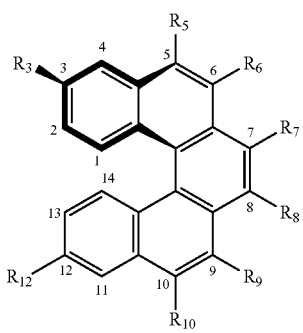

Depend on the substitutions, Rs, there are many synthetic pathways for preparation of [5]helicene compounds. 7,8-Dicyano[5]helicene compounds were prepared as precursors for phthalocyanine synthesis. [Sooksimuang et al, Porphyrins and Phthalocyanines 6(2002) 544-547 and Mandal et al, Porphyrins and Phthalocyanines 10(2006) 140-146] The studies showed the resulting phthalocyanines were soluble because of the out-of-plane structure of helicene. The studies, however, did not explain the optical properties of dicyano[5]helicene compounds. The representative of the said compound is demonstrated below.

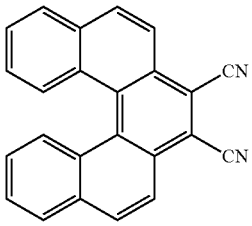 [SMILES: N#Cc1c(C#N)c2ccc3ccccc3c2c2c1ccc1ccccc12]

Because cyano is a good electron withdrawing group, the direction of electron delocalization within 7,8-dicyano[5]helicene molecule points toward cyano group. Thus, addition of electron donating groups at proper positions provided many novel organic compounds that emit light at various wavelengths with high efficiency. Many compounds were prepared and utilized as emitting layer for organic light-emitting diode as described in the following inventions.

Thai patent applications number 0601006279, 1001001071, 1001001072, 1001001426 and 1101002049 showed the addition of various functional groups to derivatives of 5,6,9,10-tetrahydro-7,8-dicyano[5]helicene compound to gain compounds having different optical and thermal properties. The compounds in these applications have optical and optoelectronic characteristics suitable for emitting materials in organic light-emitting diode. The said compounds were utilized for blue, green and yellow diodes. The chemical structures of the compounds are demonstrated below.

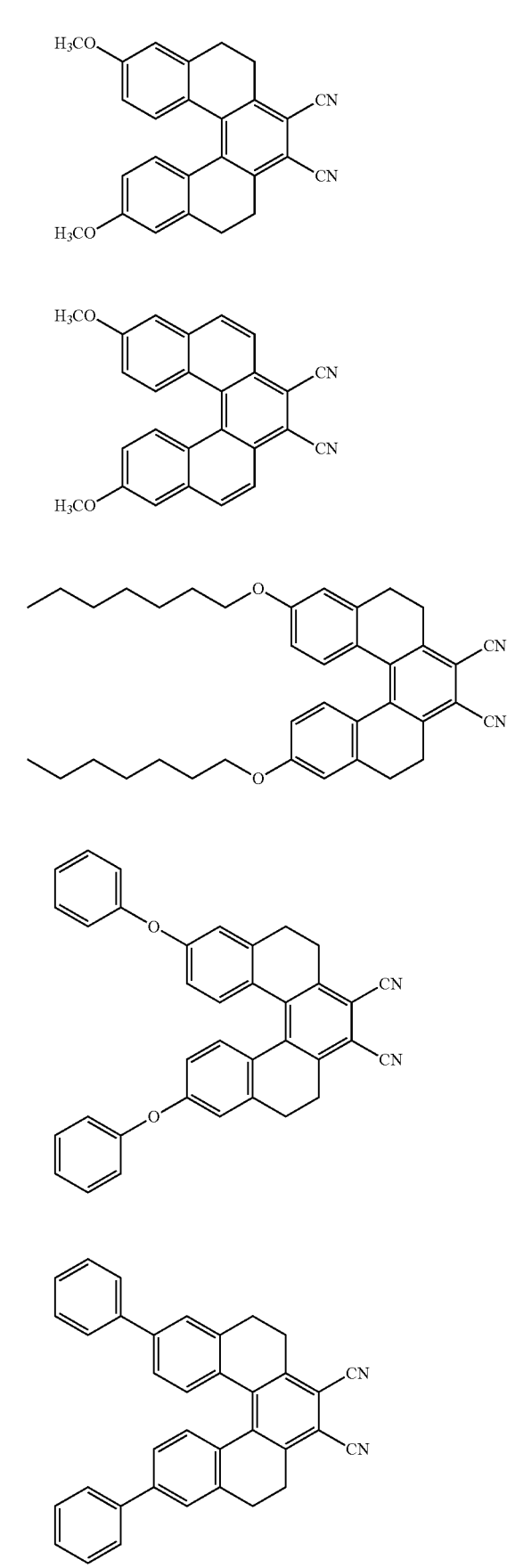 [SMILES: COc1ccc2c(c1)CCc1c(C#N)c(C#N)c3c(c1-2)-c1ccc(OC)cc1CC3 ; COc1ccc2c(ccc3c(C#N)c(C#N)c4ccc5cc(OC)ccc5c4c32)c1 ; CCCCCCCOc1ccc2c(c1)CCc1c(C#N)c(C#N)c3c(c1-2)-c1ccc(OCCCCCCC)cc1CC3 ; N#Cc1c(C#N)c2c(c3c1CCc1cc(Oc4ccccc4)ccc1-3)-c1ccc(Oc3ccccc3)cc1CC2 ; N#Cc1c(C#N)c2c(c3c1CCc1cc(-c4ccccc4)ccc1-3)-c1ccc(-c3ccccc3)cc1CC2]

-continued

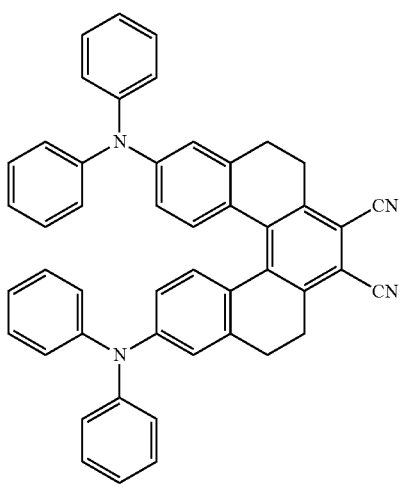 [SMILES: N#Cc1c(C#N)c2c(c3c1CCc1cc(N(c4ccccc4)c4ccccc4)ccc1-3)-c1ccc(N(c3ccccc3)c3ccccc3)cc1CC2]

Moreover, [5]helicene derivative compounds were further developed to gain broader garmut emission by changing the electron withdrawing group from cyano to anhydride and imide as appeared in Thai patent applications number 0901003446, 1201005097, 1201005098 and 1501006011. The structures of the compounds are showed as following.

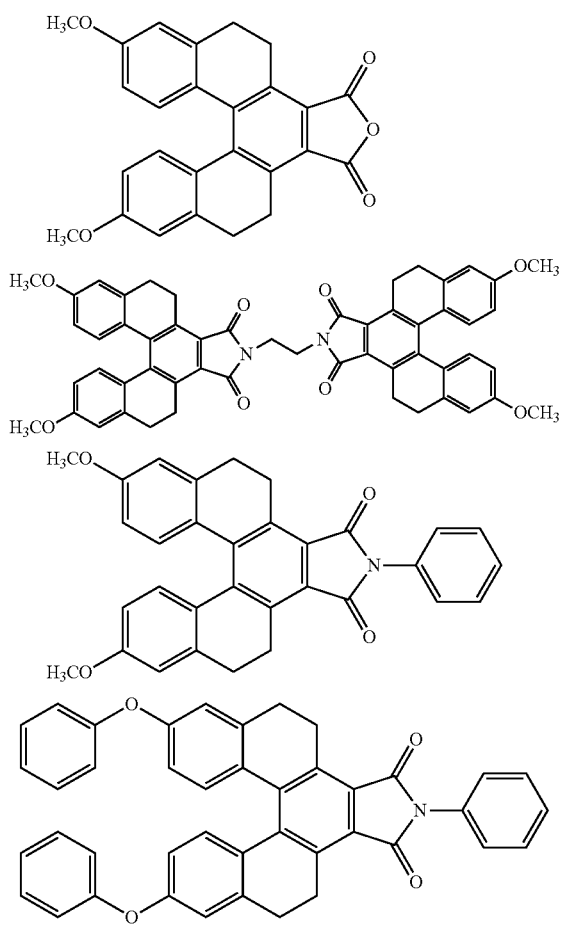

The compounds in above applications have good optical, optoelectronic and thermal characteristics suitable for emitting materials in organic light-emitting diode. Therefore, the said compounds were utilized for green diodes with good efficiencies.

2-(2-(bis(pyridin-2-yl-methyl)amino)ethyl)-7,12-dimethoxy-4,5,14,15-tetrahydro-1H-dinaphtho[2,1-e:1',2'-g]isoindole-1,3(2H)-dione, a [5]helicene derivative, was prepared and used as a chemical sensor. The molecule composes of an ionophore which able to analyze either copper or zinc ion specifically by applying different diagnostic conditions. [5]helicene fragment works as a fluorophore which makes the molecule emits fluorescent signal. The said compound was described in the Thai patent application number 1501003213 and the structure is depicted below.

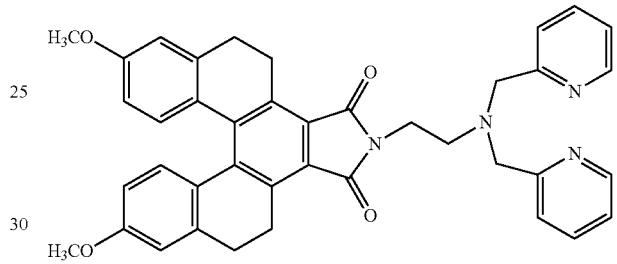

Due to the [5] helicene derivative compounds described above have many good characteristics, i.e., various visible emission wavelengths with high efficiencies, high thermal stability and good chemical resistance, the said compounds meet criteria for emissive layer in organic light-emitting diode.

Though, the structures of the said [5]helicene compounds are further modified to present different structures and properties to meet requirements for reporter molecule in biotechnology.

DETAIL DESCRIPTION OF THE INVENTION

Figure 1:
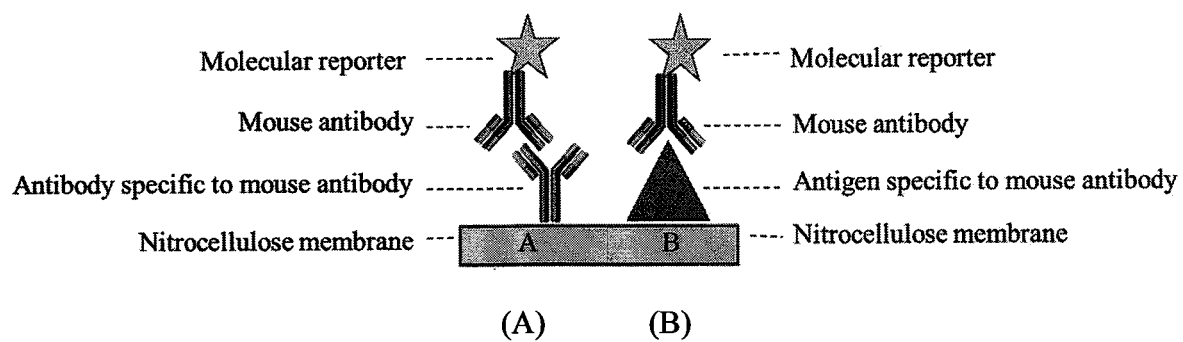
FIG. 1. Schematic of testing of the molecular reporter molecule conjugated to biomolecules such as antibody or protein.

The present invention provides [5]helicene derivative compounds represented by the following chemical formula (1):

(1)

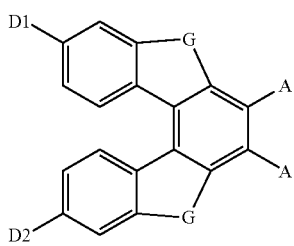

wherein
G is a connecting group composes of 2 carbon atoms selected from the group consisting of
Ethane

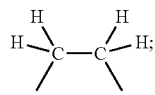

and
Ethylene

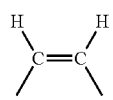

A is a separated or connected group selected from the group consisting of
Cyano
—CN; and
Imide

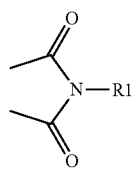

wherein R1 is selected from the group consisting of
Phenyl

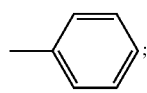

Alkyl

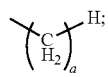

when a is a number of carbon atoms in aliphatic hydrocarbon selected from the group consisting of straight chain and branch chain, and a equals to 1 to 7; and Alkanoic acid

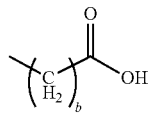

when b is a number of carbon atoms in aliphatic hydrocarbon selected from the group consisting of straight chain and branch chain, and b equals to 1 to 7.
D1 is selected from the group consisting of
Oxyalkanoic acid

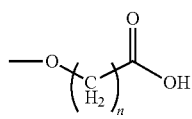

when n is a number of carbon atoms in aliphatic hydrocarbon selected from the group consisting of straight chain and branch chain, and n equals to 1 to 7;
Oxyalkanal

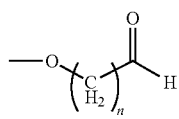

when n is a number of carbon atoms in aliphatic hydrocarbon selected from the group consisting of straight chain and branch chain and n equals to 1 to 7; and
Oxyalkanesulfonate

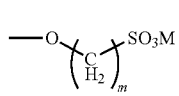

when M is a metal atom selected from the group consisting of sodium and potassium,
m is a number of carbon atoms in aliphatic hydrocarbon, selected from the group consisting of straight chain and branch chain, with a sulfonate end-group and m equals to 3 or 4.
D2 is selected from the group consisting of
Hydroxy
—OH;
Oxyalkanoic acid

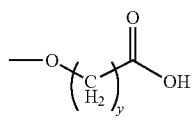

when y is a number of carbon atoms in aliphatic hydrocarbon selected from the group consisting of straight chain and branch chain, and y equals to 1 to 7;

Oxyalkanal

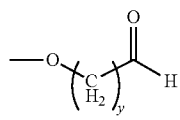

when y is a number of carbon atoms in aliphatic hydrocarbon selected from the group consisting of straight chain and branch chain, and y equals to 1 to 7;

Alkyl oxyalkanoate

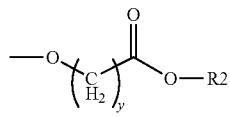

when y is a number of carbon atoms in aliphatic hydrocarbon selected from the group consisting of straight chain and branch chain, and y equals to 1 to 7, R2 is selected from the group consisting of methyl and ethyl group;

Oxyalkanol

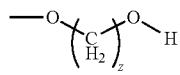

when z is a number of carbon atoms in aliphatic hydrocarbon selected from the group consisting of straight chain and branch chain, and z equals to 2 to 8; and Oxyalkanesulfonate

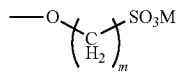

when M is a metal atom selected from the group consisting of sodium or potassium, m is a number of carbon atoms in aliphatic hydrocarbon, selected from the group consisting of straight chain and branch chain, with a sulfonate end-group and m equals to 3 or 4.

The other embodiment in this invention relates to [5]helicene derivative compounds represented in chemical formula (1) wherein a) A is cyano; G is ethane; D1 is hydroxy; and D2 is selected from the group consisting of oxyalkanoic acid and oxyalkanal.

b) A is cyano; G is ethane; D1 is oxyalkanoic acid; and D2 is selected from the group consisting of hydroxy, oxyalkanoic acid and oxyalkanesulfonate.

c) A is cyano; G is ethane; D1 is oxyalkanal; and D2 is selected from the group consisting of hydroxy, alkyl oxyalkanoate, oxyalkanal and oxyalkanol.

d) A is cyano; G is ethylene; D1 is oxyalkanoic acid; and D2 is selected from the group consisting of hydroxy, oxyalkanoic acid and oxyalkanesulfonate.

e) A is cyano; G is ethylene; D1 is oxyalkanal; and D2 is selected from the group consisting of hydroxy and oxyalkanol.

f) A is imide wherein R1 is selected from the group consisting of phenyl and alkyl; G is selected from the group consisting of ethane and ethylene; D1 is oxyalkanal; and D2 is selected from the group consisting of hydroxy, oxyalkanal, alkyl oxyalkanoate, oxyalkanol and oxyalkanesulfonate.

g) A is imide wherein R1 is alkanoic acid; G is ethane; D1 and D2 are oxyalkanesulfonate.

An example of [5]helicene derivative compounds, wherein G is ethane, A is cyano, D1 is 6-oxyhexanoic acid and D2 is hydroxyl, is 6-((3,4-dicyano-8-hydroxy-1,2,5,6-tetrahydro dibenzo[c,g]phenanthren-13-yl)oxy)hexanoic acid namely compound 1 represented by the following structure:

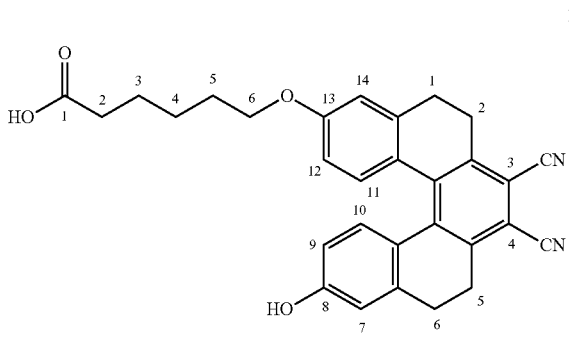

An example of [5]helicene derivative compounds, wherein G is ethane, A is cyano, D1 is 6-oxyhexanoic acid and D2 is sodium 3-oxypropane-1-sulfonate, is sodium 3-((13-((5-carboxypentyl)oxy)-3,4-dicyano-1,2,5,6-tetrahydrodibenzo[c,g]phenanthren-8-yl)oxy) propane-1-sulfonate namely compound 2 represented by the following structure:

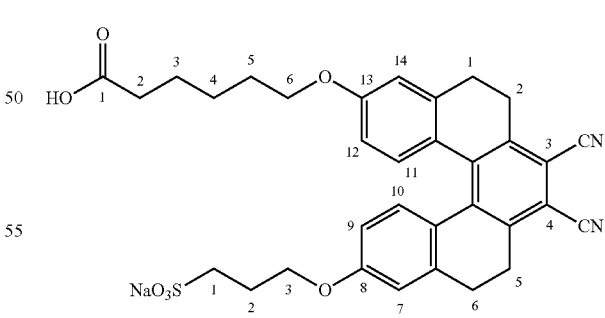

An example of [5]helicene derivative compounds, wherein G is ethane, A is cyano, D1 and D2 are 6-oxyhexanoic acid, is 6,6'-((3,4-dicyano-1,2,5,6-tetrahydrodibenzo[c,g]phenanthrene-8,13-diyl)bis(oxy))di hexanoic acid namely compound 3 represented by the following structure:

3

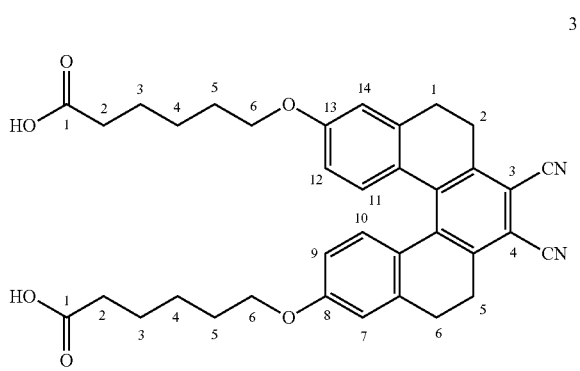 [SMILES: N#Cc1c(C#N)c2c(c3c1CCc1cc(OCCCCCC(=O)O)ccc1-3)-c1ccc(OCCCCCC(=O)O)cc1CC2]

An example of [5]helicene derivative compounds, wherein G is ethylene, A is cyano, D1 is 6-oxyhexanoic acid and D2 is hydroxy, is 6-((3,4-dicyano-8-hydroxydibenzo[c,g]phenanthren-13-yl)oxy)hexanoic acid namely compound 4 represented by the following structure:

4

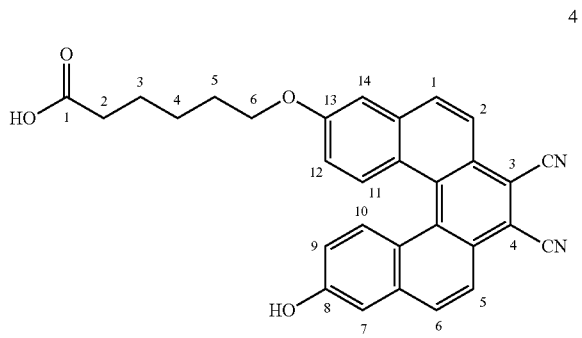 [SMILES: N#Cc1c(C#N)c2ccc3cc(OCCCCCC(=O)O)ccc3c2c2c1ccc1cc(O)ccc12]

An example of [5]helicene derivative compounds, wherein G is ethylene, A is cyano, D1 is 6-oxyhexanoic acid and D2 is sodium 3-oxypropane-1-sulfonate, is sodium 3-((8-((5-carboxypentyl)oxy)-3,4-dicyanodibenzo[c,g]phenanthren-13-yl)oxy)propane-1-sulfonate namely compound 5 represented by the following structure:

5

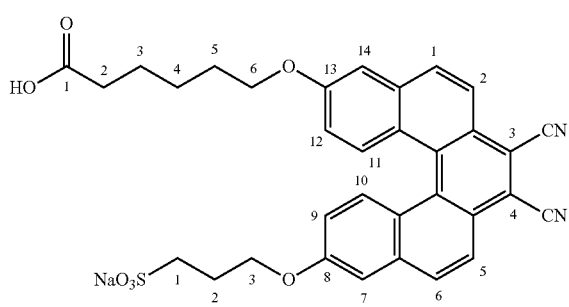

An example of [5]helicene derivative compounds, wherein G is ethylene, A is cyano, D1 and D2 are 6-oxyhexanoic acid, is 6,6'-((3,4-dicyanodibenzo[c,g]phenanthrene-8,13-diyl)bis(oxy))dihexanoic acid namely compound 6 represented by the following structure:

6

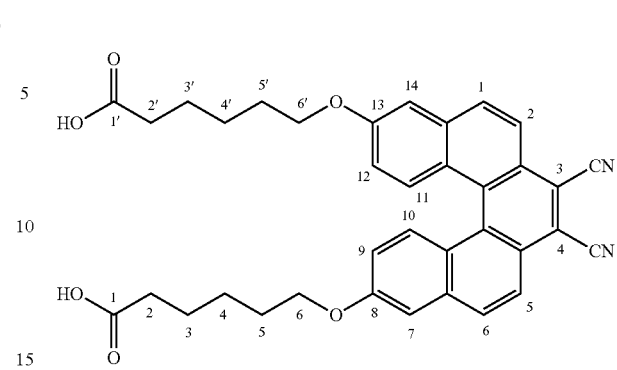

An example of [5]helicene derivative compounds, wherein G is ethane, A is cyano, D1 is 6-oxyhexanal and D2 is hydroxy, is 8-hydroxy-13-((6-oxohexyl)oxy)-1,2,5,6-tetrahydro dibenzo[c,g]phenanthrene-3,4-dicarbonitrile namely compound 7 represented by the following structure:

7

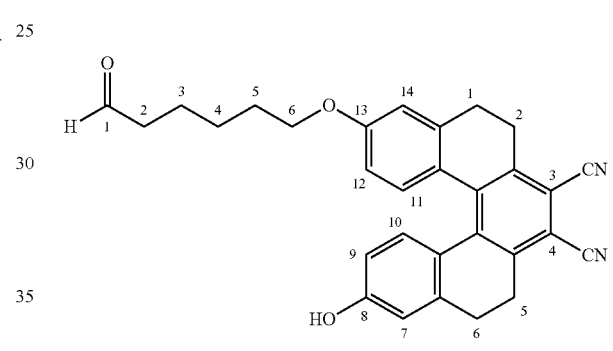

An example of [5]helicene derivative compounds, wherein G is ethane, A is cyano, D1 and D2 are 6-oxyhexanal, is 8,13-bis((6-oxohexyl)oxy)-1,2,5,6-tetrahydrodibenzo[c,g]phenanthrene-3,4-dicarbonitrile namely compound 8 represented by the following structure:

8

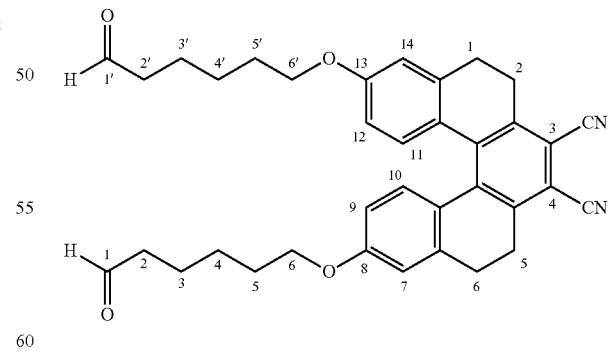

An example of [5]helicene derivative compounds, wherein G is ethane, A is cyano, D1 is 6-oxyhexanal and D2 is 6-oxyhexan-1-ol, is 8-((6-hydroxyhexyl)oxy)-13-((6-oxohexyl)oxy)-1,2,5,6-tetrahydrodibenzo[c,g]phenanthrene-3,4-dicarbonitrile namely compound 9 represented by the following structure:

9

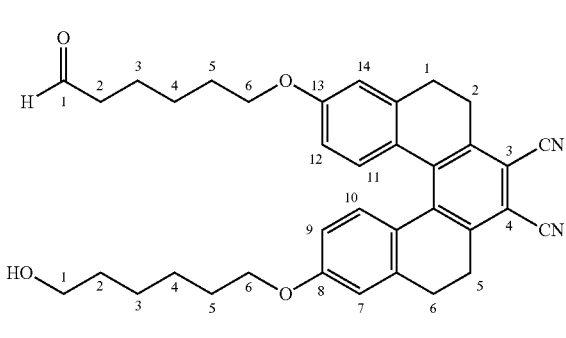

An example of [5]helicene derivative compounds, wherein G is ethane, A is cyano, D1 is 4-oxybutanal and D2 is ethyl 4-oxybutanoate, is ethyl 4-((3,4-dicyano-13-(4-oxobutoxy)-1,2,5,6-tetrahydrodibenzo[c,g]phenanthren-8-yl)oxy)butanoate namely compound 10 represented by the following structure:

10

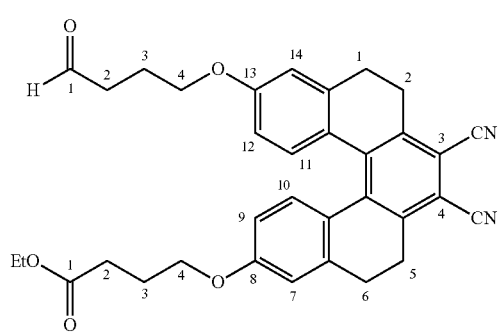

An example of [5]helicene derivative compounds, wherein G is ethylene, A is cyano, D1 is 6-oxyhexanal and D2 is hydroxy, is 8-hydroxy-13-((6-oxohexyl)oxy)dibenzo[c,g]phenanthrene-3,4-dicarbonitrile namely compound 11 represented by the following structure:

11

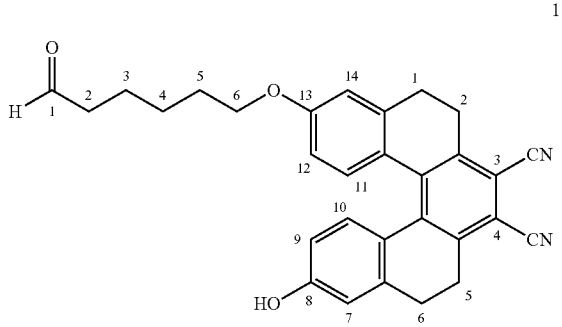

An example of [5]helicene derivative compounds, wherein G is ethylene, A is cyano, D1 and D2 are 6-oxyhexanal, is 8,13-bis((6-oxohexyl)oxy)dibenzo[c,g]phenanthrene-3,4-dicarbonitrile namely compound 12 represented by the following structure:

12

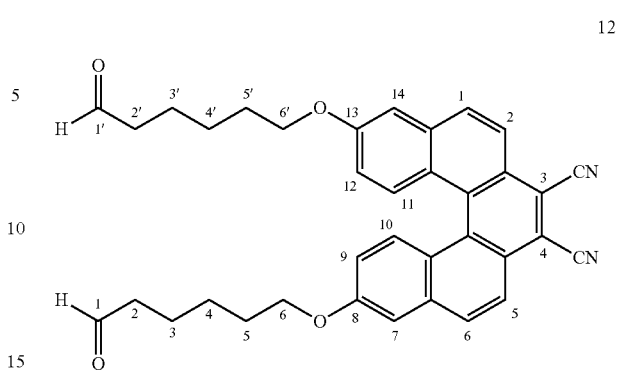

An example of [5]helicene derivative compounds, wherein G is ethane, A is imide wherein R1 is 4-butanoic acid, D1 and D2 are sodium 3-oxypropane-1-sulfonate, is sodium 3,3'-((2-(3-carboxypropyl)-1,3-dioxo-4,5,14,15-tetrahydro-1H-dinaphtho[2,1-e:1',2'-g]isoindole-7,12-diyl) bis(oxy))bis(propane-1-sulfonate) namely compound 13 represented by the following structure:

13

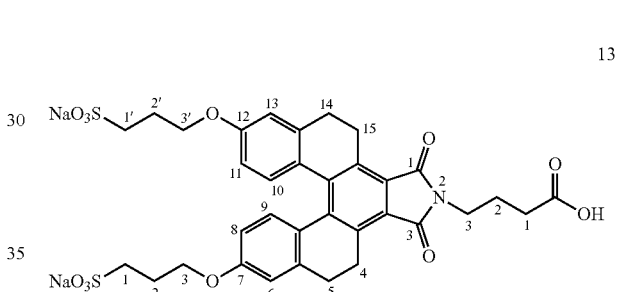

An example of [5]helicene derivative compounds, wherein G is ethane, A is imide wherein R1 is phenyl, D1 is 6-oxyhexanal and D2 is sodium 3-oxypropane-1-sulfonate, is sodium 3-((1,3-dioxo-12-((6-oxohexyl)oxy)-2-phenyl-4,5,14,15-tetrahydro-1H-dinaphtho[2,1-e:1',2'-g]isoindol-7-yl)oxy)propane-1-sulfonate namely compound 14 represented by the following structure:

14

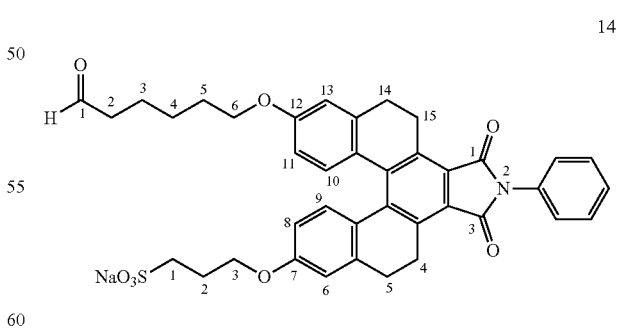

An example of [5]helicene derivative compounds, wherein G is ethane, A is imide wherein R1 is phenyl, D1 is 6-oxyhexanal and D2 is hydroxy, is 6-((7-hydroxy-1,3-dioxo-2-phenyl-4,5,14,15-hexahydro-1H-dinaphtho[2,1-e:1',2'-g]isoindol-12-yl)oxy)hexanal namely compound 15 represented by the following structure:

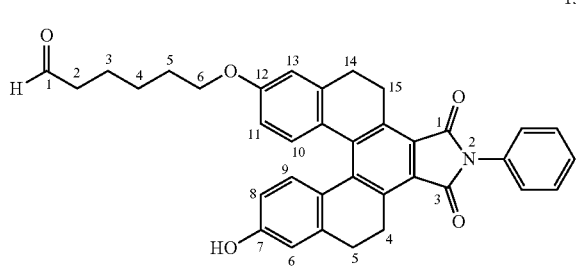

15

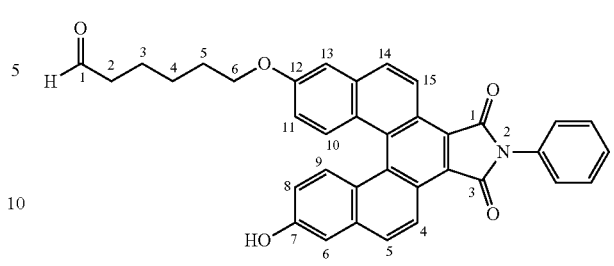

18

An example of [5]helicene derivative compounds, wherein G is ethane, A is imide wherein R1 is phenyl, D1 and D2 are 6-oxyhexanal, is 6,6'-(((1,3-dioxo-2-phenyl-2,3,4,5,14,15-hexahydro-1H-dinaphtho[2,1-e:1',2'-g]isoindole-7,12-diyl)bis(oxy))dihexanal namely compound 16 represented by the following structure:

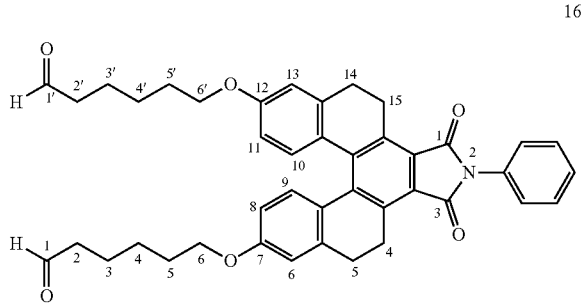 [SMILES: O=CCCCCCOc1ccc2c(c1)CCc1c3c(c4c(c1-2)-c1ccc(OCCCCCC=O)cc1CC4)C(=O)N(c1ccccc1)C3=O]

16

An example of [5]helicene derivative compounds, wherein G is ethane, A is imide wherein R1 is phenyl, D1 is 6-oxyhexanal and D2 is ethyl 6-oxyhexanoate, is ethyl 6-((1,3-dioxo-12-((6-oxohexyl)oxy)-2-phenyl-4,5,14,15-tetraahydro-1H-dinaphtho[2,1-e:1',2'-g] isoindol-7-yl)oxy) hexanoate namely compound 17 represented by the following structure:

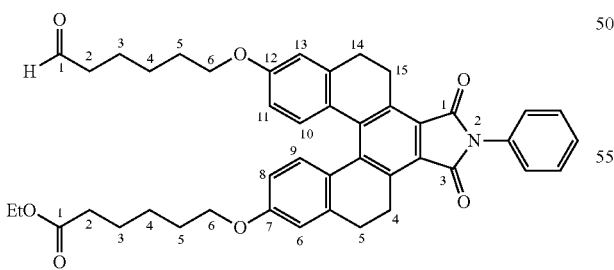

17

An example of [5]helicene derivative compounds, wherein G is ethylene, A is imide wherein R1 is phenyl, D1 is 6-oxyhexanal and D2 is hydroxy, is 6-((7-hydroxy-1,3-dioxo-2-phenyl-1H-dinaphtho[2,1-e:1',2'-g]isoindol-12-yl)oxy)hexanal namely compound 18 represented by the following structure:

The derivative of [5]helicene compounds in the present invention compose of aromatic [5]helicene core comprising long π-conjugating system. Owing to having proper chemical structure, the compounds in the present invention exhibit good fluorescence. Moreover, the said compounds contain functional groups which able to link with biomolecule and they are soluble in water or other solvents that used in binding process with biomolecules. The said compounds give fluorescent emission in the range of 425-675 nm. When the said compounds connected with biomolecules such as protein, antibody and peptide, the biomolecules give good fluorescent emission which can be detected under ultraviolet radiation. Because of their good chemical and optical properties, the luminescent organic compounds in the present invention are suitable for utilizing as reporter molecules in diagnostic for microbials, toxins and toxicants in samples from agricultural industries, foods and environments.

In an embodiment, there is described an intermediate compound for preparation of the [5]helicene derivative compounds, having the chemical formula:

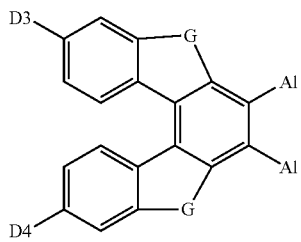

wherein,

G is a connecting group comprising 2 carbon atoms selected from the group consisting of Ethane

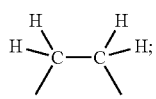

and

Ethylene

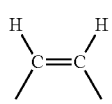

A1 is a separated or connected group selected from the group consisting of

Cyano

—CN; and

Imide

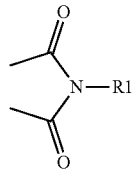

wherein R1 is selected from the group consisting of

Phenyl

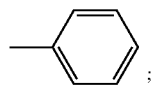;

Alkyl

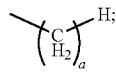

when a is a number of carbon atoms in aliphatic hydrocarbon and a equals to 1 to 7; and Alkanoic acid

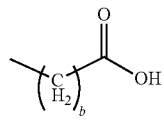

when b is a number of carbon atoms in aliphatic hydrocarbon, b equals to 1 to 7;

D3 is selected from the group consisting of

Hydroxy

—OH; and

Alkyl oxyalkanoate

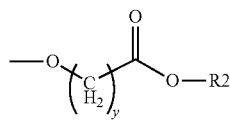

when y is an aliphatic hydrocarbon containing 1 to 7 carbon atoms,

R2 is selected from the group consisting of methyl and ethyl group

D4 is selected from the group consisting of

Hydroxy

—OH;

Oxyalkanoic acid

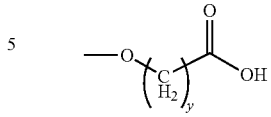

when y is a number of carbon atoms in aliphatic hydrocarbon and y equals to 1 to 7;

Oxyalkanal

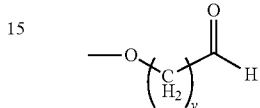

when y is a number of carbon atoms in aliphatic hydrocarbon and y equals to 1 to 7;

Alkyl oxyalkanoate

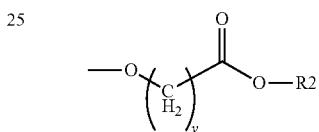

when y is a number of carbon atoms in aliphatic hydrocarbonand y equals to 1 to 7, R2 is selected from the group consisting of methyl and ethyl group;

Oxyalkanol

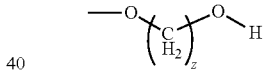

when z is a n her of carbon atoms in aliphatic hydrocarbonand z equals to 2 to 8; and Oxyalkanesulfonate

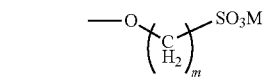

when M is a metal atom selected from the group consisting of sodium and potassium, m is a number of carbon atoms in aliphatic hydrocarbon and in equals to 3 or 4.

In an embodiment, in the intermediate compowid described herein the alkanoic acid at the A1 position of the imide group is straight chain or branched chain.

In an embodiment, in the intermediate compowid described herein, the alkyl oxyalkanoate at the D3 position is straight chain or branched chain.

In an embodiment of the intermediate compound described herein, at the D4 position:

the oxvalkanoic acid is straight chain or branched chain;
the oxyalkanol is straight chain or branched chain;
the alkyl oxyalkanoate is straight chain or branched chain;
the oxyalkanol is straight chain or branched chain; and
the oxvalkanesulfonate is straight chain or branched chain.

The methods of Synthesis for [5]Helicene Derivative Compounds in the Present Invention Comprise Steps of:

a.) An O-alkylation reaction (to incorporate an alkylester) of the [5]helicene compound in formula (4), selected from the [5]helicene compound in formula (4) wherein A1 is imide or the [5]helicene compound in formula (4) wherein A1 is cyano, with haloalkanoic acid alkyl ester (I) which is a primary alkyl halide containing a desired ester end group. The said reaction is performed in the present of base 1, as a catalyst, selected from the group consisting of sodium bicarbonate ($NaHCO_3$), potassium bicarbonate ($KHCO_3$), sodium carbonate ($Na_2CO_3$) and potassium carbonate ($K_2CO_3$) and the most effective is potassium carbonate ($K_2CO_3$). Also, the said alkylation is done in organic solvent 1 selected from the group consisting of dimethyl formamide, acetone, acetonitrile and mixture thereof wherein the most effective solvent is dimethyl formamide. The reaction is carried on at the temperature in the range of 60-160° C. for the period of 2-12 hours to give [5]helicene compound (5) and/or compound (6) as intermediate molecule containing at least one alkylester group. The reaction is depicted below.

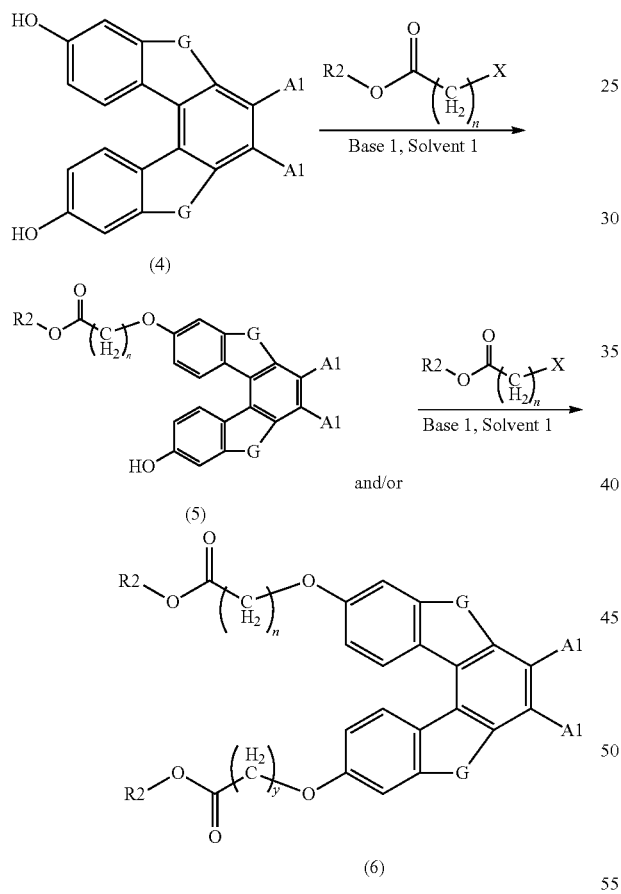

wherein n and y are indepent at which
n is a number of carbon atoms of aliphatic hydrocarbon in haloalkanoic acid alkyl ester (I) reacting in the first alkylation reaction where n equals to 1 to 7 and the said hydrocarbon is selected from the group consisting of straight chain and branch chain.
y is a number of carbon atoms of aliphatic hydrocarbon in haloalkanoic acid alkyl ester (I) reacting in the second alkylation reaction where y equals to 1 to 7 and the said hydrocarbon is selected from the group consisting of straight chain and branch chain.

X is halogen atom selected from the group consisting of chlorine(Cl), bromine(Br) and iodine(I).
R2 is alkyl group selected from the group consisting of methyl and ethyl.
G is a connecting group composes of 2 carbon atoms selected from the group consisting of
Ethane

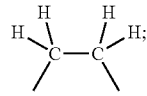

and
Ethylene

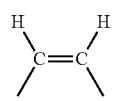

A1 is a separated or connected group selected from the group consisting of
Cyano
—CN; and
Imide

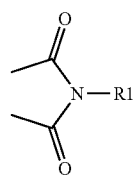

wherein R1 is selected from the group consisting of
Phenyl

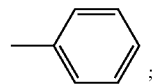

;

Alkyl

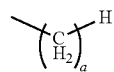

when a is a number of carbon atoms in aliphatic hydrocarbon selected from the group consisting of straight chain and branch chain, and a equals to 1 to 7; and
Alkanoic acid

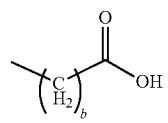

when b is a number of carbon atoms in aliphatic hydrocarbon selected from the group consisting of straight chain and branch chain, and b equals to 1 to 7.

b.) A hydrolysis reaction of [5]helicene compound (5) or compound (6) using base 2 selected from the group consisting of sodium hydroxide (NaOH), potassium hydroxide (KOH) and lithium hydroxide (LiOH). The reaction is performed in an organic solvent 2 selected from the group consisting of ethanol, methanol, tetrahydrofuran, dioxane, dichloromethane and a mixture thereof wherein the most effective solvent is ethanol. The said reaction is carried out at temperature in the range of 25-150° C. for 1-24 hours, follow by acidify with acid 1, selected from the group consisting hydrochloric acid and sulfuric acid, to gain pH 0 to obtain [5]helicene compound (7) or compound (8) which contains at least one carboxylic group as a final product or an intermediate. The reaction is depicted below.

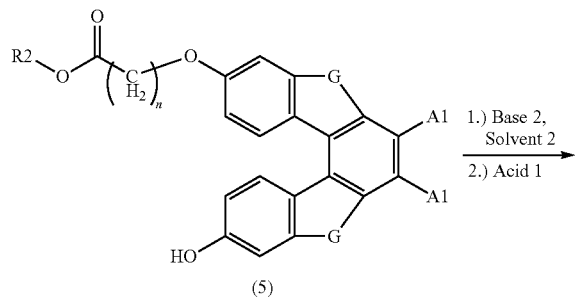

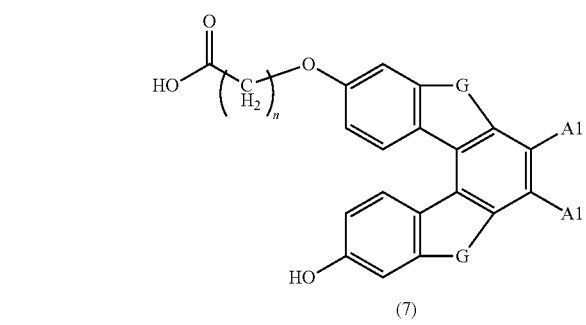

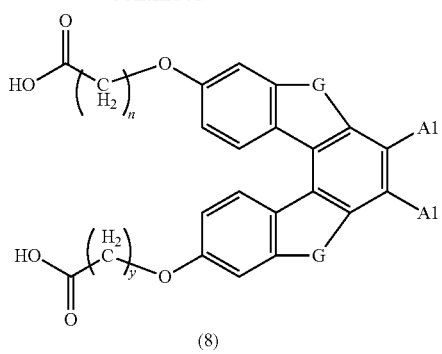

c.) An O-alkylation reaction for addition of sulfonate group to the molecule and make the molecule soluble in aqueos media. The intermediate compound containing OH group, selected from of [5]helicene compound (4), compound (5) or compound (7) reacts with alkane sultone) (II) at the present of base 3 as a catalyst, selected from the group consisting of sodium hydroxide (NaOH), potassium hydroxide (KOH), sodium methoxide (NaOMe), potassium methoxide (KOMe), sodium ethoxide (NaOEt) and potassium ethoxide (KOEt) wherein the most effective is sodium ethoxide. An organic solvent 3 selected from the group consisting of methanol, ethanol, acetone and acetonitrile is used as solvent in this reaction and the most effective is ethanol. The reaction is carried out at temperature in the range of 25-80° C. for 6 to 120 hours to obtain [5]helicene compound (9), compound (10) or compound (11) as final product of intermediate. The reaction is presented as following;

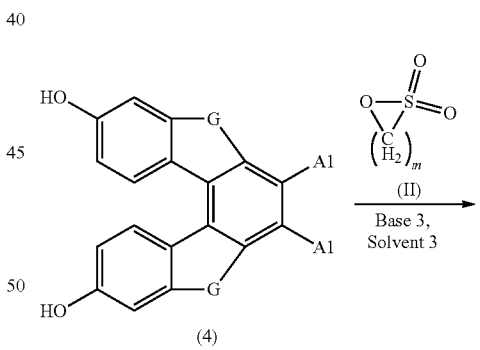

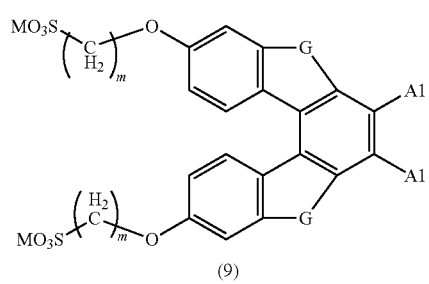

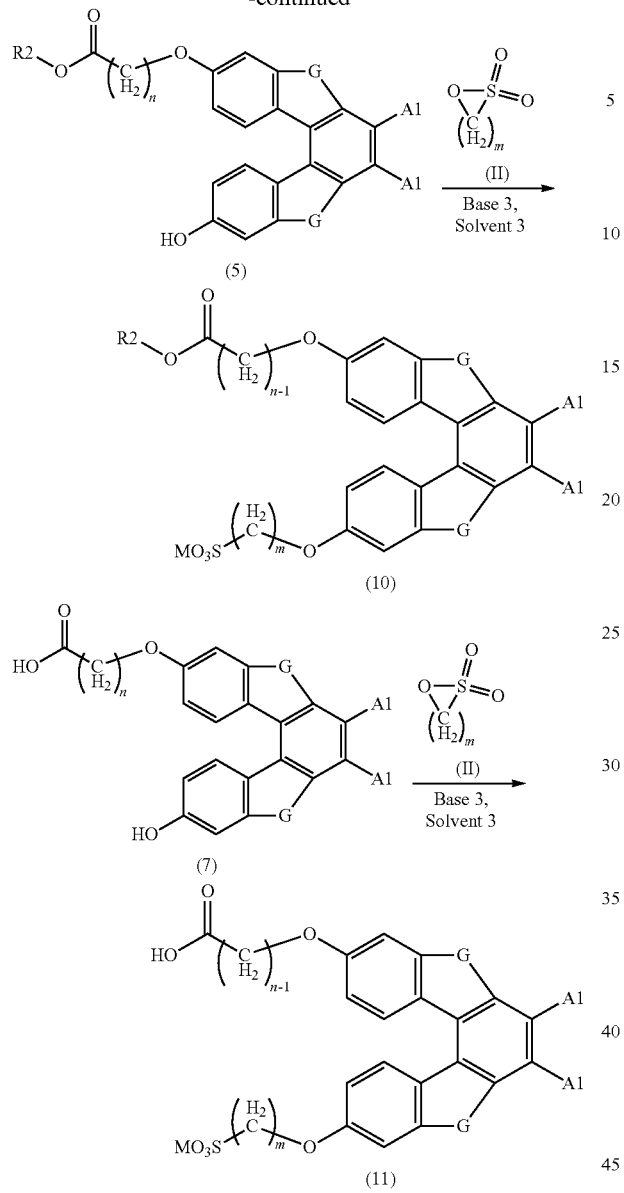

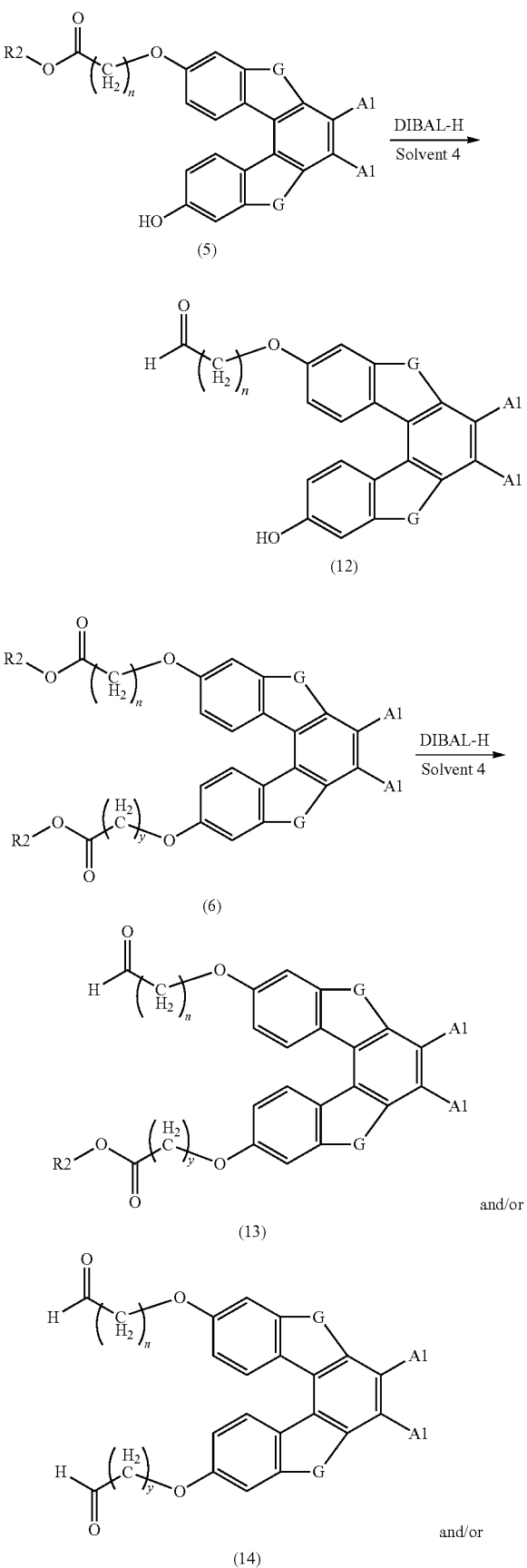

wherein

M is a metal atom selected from the group consisting of sodium and potassium, m is a number of carbon atoms in aliphatic hydrocarbon, selected from the group consisting of straight chain and branch chain and m equals to 3 or 4.

d.) A reduction reaction of intermediate containing ester group, selected from [5]helicene compound (5), compound (6) or compound (10), using diisobutylaluminum hydride, (DIBAL-H). The reaction is performed in an organic solvent 4 selected from the group consisting of dichloromethane, tetrahydrofuran, toluene and a mixture thereof. The reaction is carried out at temperature in the range of −90° C. to room temperature for 1-4 hours to gain [5]helicene compound (12), compound (13) and/or compound (14) and/or compound (15) or compound (16) as final product.

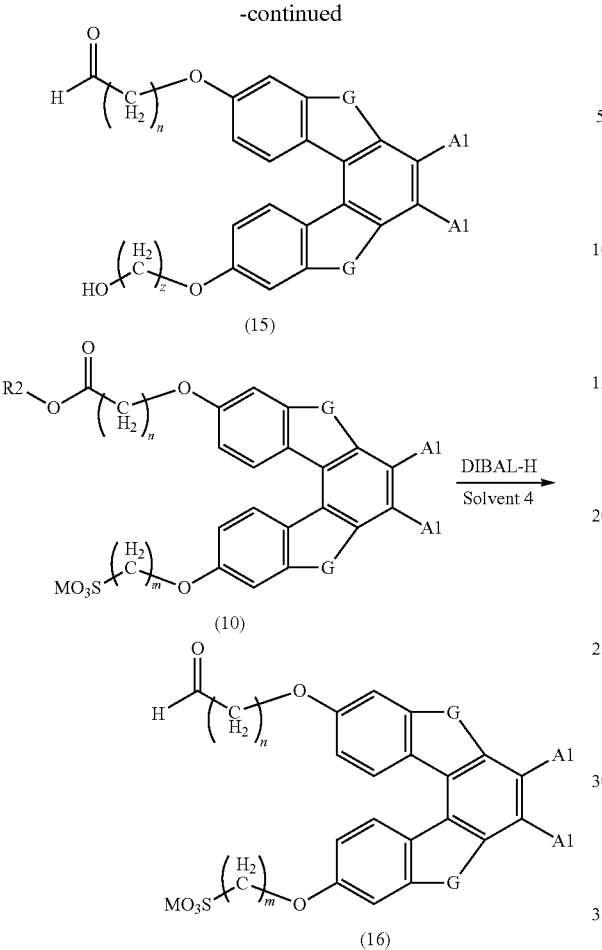

(15)

(10)

(16)

wherein m, n, y and z are independent when
n is a number of carbon atoms in aliphatic hydrocarbon selected from the group consisting of straight chain and branch chain and n equals to 1 to 7,
y number of carbon atoms in aliphatic hydrocarbon selected from the group consisting of straight chain and branch chain and y equals to 1 to 7,
z is a number of carbon atoms in aliphatic hydrocarbon selected from the group consisting of straight chain and branch chain and z equals to 1 to 7,
M is a metal atom selected from the group consisting of sodium or potassium,
m is a number of carbon atoms in aliphatic hydrocarbon, selected from the group consisting of straight chain and branch chain, with a sulfonate end-group and m equals to 3 or 4.

Furthermore, the synthesis of organic dyes based on [5]helicene derivative compounds in this invention comprises imidation reaction to make imide compound. The said reaction is done by reacting [5]helicene compound in formula (2) with a primary amine (III) in the present of acid 2 as a catalyst selected from the group consisting of acetic acid, hydrochloric acid and sulfuric acid and the most effective is acetic acid. The reaction is performed in an organic solvent 5 selected from the group consisting of dimethyl formamide, dimethyl sulfoxide, acetonitrile, toluene, benzene and a mixture thereof and the most effective solvent is dimethyl formamide. The reaction is carried out at temperature in the range of 80 to 160° C. for 2 to 12 hours to gain [5]helicene isoindole dione compound represented by the chemical formula (3) and the reaction is depicted as following.

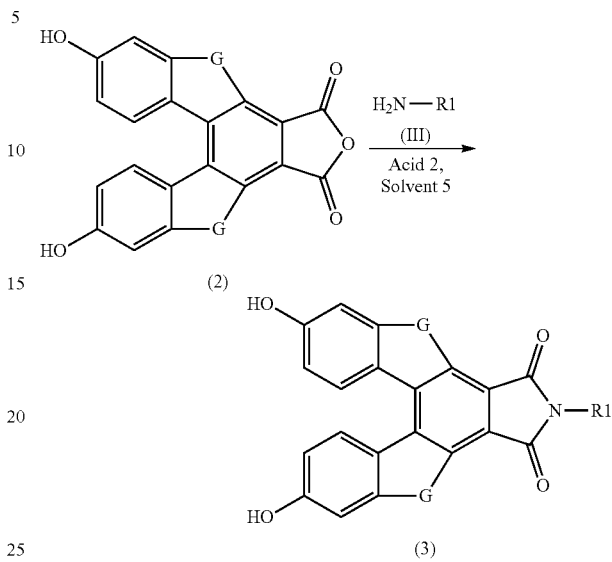

(2)

(3)

wherein
G is a connecting group composes of 2 carbon atoms selected from the group consisting of
Ethane

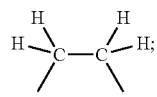

and
Ethylene

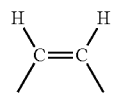

wherein R1 is selected from the group consisting of
Phenyl

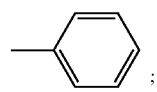

;

Alkyl

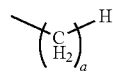

when a is a number of carbon atoms in aliphatic hydrocarbon selected from the group consisting of straight chain and branch chain and a equals to 1 to 7; and Alkanoic acid

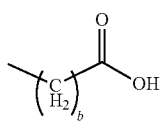

when b is a number of carbon atoms in aliphatic hydrocarbon selected from the group consisting of straight chain and branch chain and b equals to 1 to 7.

Nonetheless, the sequences of reaction steps for preparation method of [5]helicene derivative compounds are alterable to obtain desired products.

The Synthesis Method of [5] Helicene Derivative Compounds in the Present Invention are Demonstrated in the Following Examples:

EXAMPLE 1

The synthesis of 6-((3,4-dicyano-13-hydroxy-1,2,5,6-tetrahydrodibenzo[c,g]phenanthren-8-yl)oxy)hexanoic acid) or compound 1
Step a)

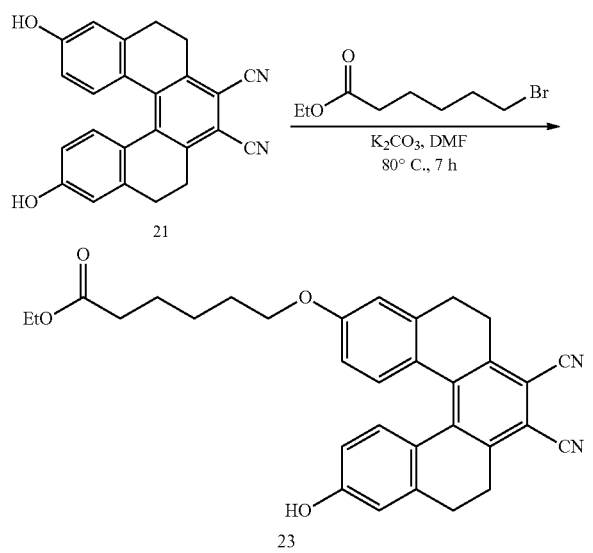

A mixture of 8,13-dihydroxy-1,2,5,6-tetrahydrodibenzo[c,g]phenanthrene-3,4-dicarbo nitrile, compound 21, (1.00 g, 2.75 mmol), ethyl-6-bromohexanolate (0.61 g, 2.75 mmol), potassium carbonate (K$_2$CO$_3$) (0.46 g, 3.30 mmol) and 50 mL of DMF in a 100 mL round-bottom flask were stirred and heated at 80° C. under argon atmosphere for 7 h. After cooling to room temperature, the reaction mixture was dumped into water (600 mL) with vigorous stirring for 1 h. The aqueous layer was extracted with ethyl acetate (200 mL×2). The organic layer was dried with Na$_2$SO$_4$ and removed to yield a crude product. The crude product was purified by normal phase column chromatography (silica gel, 20% to 50% EtOAc-Hexane) to give pure ethyl 6-((3, 4-dicyano-13-hydroxy-1,2,5,6-tetrahydrodibenzo[c,g] phenanthren-8-yl)oxy)hexanoate, compound 23, as yellow viscous liquid (0.8 g, 57% yield). This compound was used for the next step.

Step b)

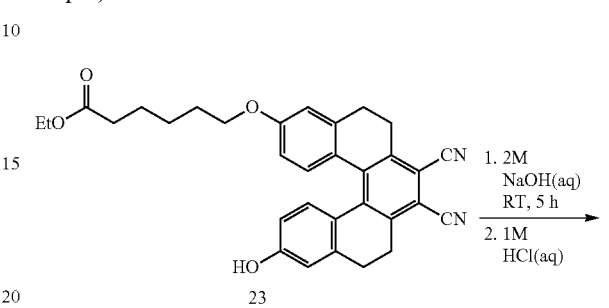

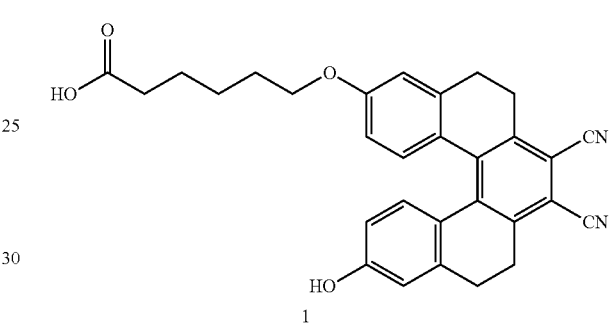

6-((3,4-Dicyano-13-hydroxy-1,2,5,6-tetrahydrodibenzo[c,g]phenanthren-8-yl)oxy) hexa noate, compound 23, (0.20 g, 0.39 mmol) was dissolved in 4.0 mL of ethanol and 1.5 mL of 2M NaOH aqueous solution was added. The solution was stirred at room temperature for 5 h. 1M HCl Aqueous solution was added to the reaction solution until pH equals to 0, resulting in a yellow-orange precipitation. The precipitated solid was washed with water and dried to gain pure product, 6-((3,4-dicyano-13-hydroxy-1,2,5,6-tetrahydrodibenzo[c,g]phenanthren-8-yl)oxy)hexanoic acid) or compound 1, as pale yellow solid (0.18 g, 95% yield).

$^1$H NMR (500 MHz, MeOD-d$_4$): δ 7.10 (d, J=8.5 Hz, 1H), 7.01 (d, J=8.5 Hz, 1H), 6.85 (s, 1H), 6.72 (s, 1H), 6.51 (d, J=7.0 Hz, 1H), 6.38 (d, J=7.0 Hz, 1H), 3.96 (s, 2H), 3.23 (s, 2H), 2.87-2.80 (m, 4H), 2.58 (s, 2H), 2.18 (t, J=7.5 Hz, 2H), 1.77-1.75 (m, 2H), 1.65-1.62 (m, 2H), 1.50-1.48 (m, 2H) ppm.

$^{13}$C NMR (125 MHz, MeOD-d$_4$): δ 183.00, 161.82, 160.32, 145.44,145.34, 142.83, 142.68, 139.35, 138.90, 132.83, 132.60, 126.99, 125.90, 117.10, 115.71, 114.97, 114.68, 114.17, 112.58, 112.37, 69.51(2×CH$_2$), 39.41(3× CH$_2$), 30.67, 30.10, 27.86, 27.66 ppm.

FT-IR (KBr): ν$_{max}$ 3363, 3212, 2943, 2224, 1705, 1606, 1411, 1274, 1242, 863, 821 cm$^{-1}$.

EXAMPLE 2

The synthesis of sodium 3-((13-((5-carboxypentyl)oxy)-3,4-dicyano-1,2,5,6-tetrahydrodibenzo[c,g]phenanthren-8-yl)oxy) propane-1-sulfonate or compound 2

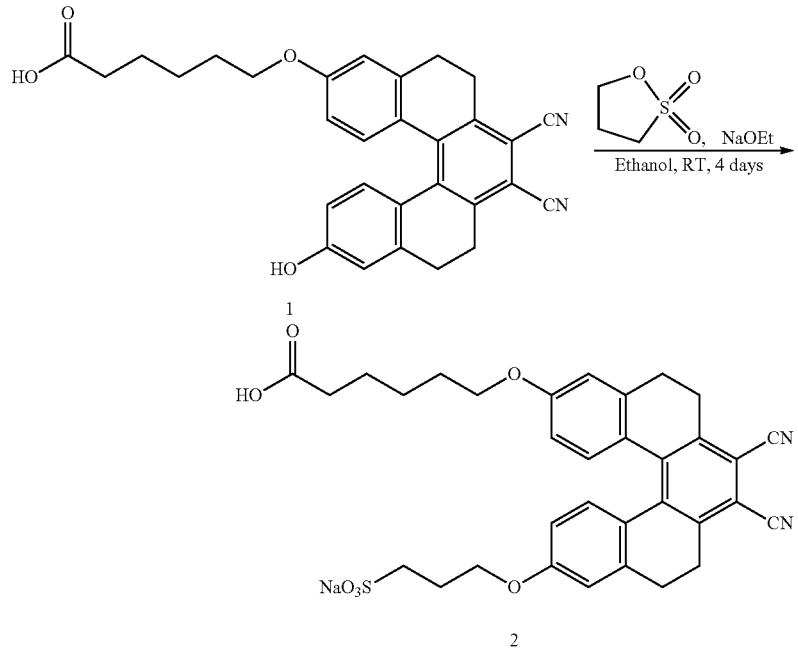

A mixture of 6-((3,4-dicyano-13-hydroxy-1,2,5,6-tetrahydrodibenzo[c,g]phenanthren-8-yl)oxy)hexanoic acid) or compound 1 (0.13 g, 0.27 mmol) in dry ethanol (5 mL) was stirred until all solids disappeared under argon atmosphere. A mixture of sodium ethoxide (0.040 g, 0.59 mmol) in 3 mL of dry ethanol was added dropwise and stirred for 1 h, causing the yellow solution to turn orange-brown. Then, 1,3 propanesultone (0.05 g, 0.44 mmol) in 2 mL of dry ethanol was added to the mixture. The reaction mixture was stirred at room temperature for 4 days. The reaction was followed by using TLC and precipitation of orange solid. Removing of ethanol by distillation under reduced pressure gave the crude product. The crude product was purified by column chromatography using reversed phased silica gel (50% to 100% MeOH:$H_2O$) to give pure product, sodium 3-((13-((5-carboxypentyl)oxy)-3,4-dicyano-1,2,5,6-tetrahydrodibenzo[c,g]phenanthren-8-yl)oxy) propane-1-sulfonate or compound 2, as yellow-green solid (0.09 g, 44% yield).

$^1$H NMR(500 MHz, MeOD-$d_4$): δ 7.10 (tt, J=7.8, 1.5 Hz, 2H), 6.90 (s, 1H), 6.87 (s, 1H), 6.54 (tt, J=10.3, 2.0 Hz, 2H), 4.11 (s, 2H), 3.97 (s, 2H), 3.30-3.25 (broad, 1H), 2.96 (t, J=7.5 Hz, 2H), 2.90 (s, 4H), 2.62 (s, 2H), 2.25-2.18 (m, 2H), 2.16 (t, J=7.5 Hz, 2H), 1.78-1.75 (m, 2H), 1.66-1.63 (m, 2H), 1.50-1.48 (m, 2H) ppm.

FT-IR(KBr): $v_{max}$ 3445, 2943, 2857, 2221, 1718, 1607, 1275, 1244, 1209, 1038, 853, 597 cm$^{-1}$.

EXAMPLE 3

The synthesis of 6,6'-((3,4-dicyano-1,2,5,6-tetrahydrodibenzo[c,g] phenanthrene-8,13-diyl)bis(oxy))dihexanoic acid or compound 3

Step a)

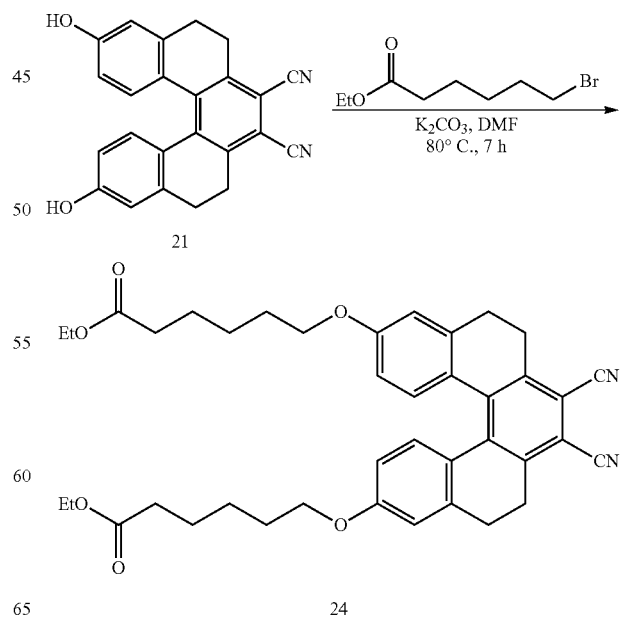

A mixture of 8,13-dihydroxy-1,2,5,6-tetrahydrodibenzo[c,g] phenanthrene-3,4-dicarbonitrile, compound 21, (0.50 g, 1.37 mmol), ethyl-4-bromobutyrate (0.67 g, 3.00 mmol), potassium carbonate ($K_2CO_3$) (0.57 g, 4.13 mmol) and 15 mL of DMF were stirred and heated at 80° C. under argon atmosphere for 7 h. After cooling to room temperature, the reaction mixture was dumped into water (600 mL) with vigorous stirring for 1 h. The aqueous layer was extracted with ethyl acetate (200 mL×2). The organic layer was dried with $Na_2SO_4$ and removed to yield a crude product. The crude product was purified by normal phase column chromatography (silica gel, 50% EtOAc-Hexane) to give pure diethyl 6,6'((3,4-dicyano-1,2,5,6-tetrahydro dibenzo[c,g] phenanthrene-8,13-diyl)bis(oxy))dihexanoate, compound 24 as yellow solid (0.82 g, 92% yield).
Step b)

Diethyl 6,6'-((3,4-dicyano-1,2,5,6-tetrahydrodibenzo[c,g] phenanthrene-8,13-diyl) bis (oxy))dihexanoate, compound 24, (0.29 g, 0.44 mmol) was dissolved in 5.0 mL of ethanol and 3 mL of 2M NaOH aqueous solution was added to the reaction mixture. The solution was stirred at room temperature for 5 h, after which ethanol was removed under reduced pressure. 1M HCl (aq) was added to the solution until pH equals to 0, resulting in an orange precipitate. The precipitate was washed with water (15 mL) and dried (0.24 g, 92% yield, mp. 172-173° C.).

$^1$H NMR (500 MHz, MeOD-$d_4$): δ 7.08 (d, J=8.5 Hz, 2H), 6.86 (s, 2H), 6.51 (d, J=7.0, 2H), 4.12 (b s, 4H), 3.30-3.20 (b, 2H), 2.95-2.85 (b, 4H), 2.70-2.52 (b, 2H), 2.30 (t, J=7.0 Hz, 4H), 1.90-1.75 (m, 4H), 1.75-1.60 (m, 4H), 1.55-1.45 (m, 4H) ppm.

$^{13}$C NMR (125 MHz, MeOD-$d_4$): δ 177.55, 161.30, 144.96, 142.28, 138.54, 132.19, 126.48, 116.54, 114.24, 113.68, 112.21, 68.88, 34.87, 30.02, 29.64, 29.58, 26.75, 25.83 ppm.

FT-IR(KBr): $\nu_{max}$ 3462, 2943, 2910, 2221, 1707, 1607, 1275, 1244, 1108, 1095, 855, 809 cm$^{-1}$.

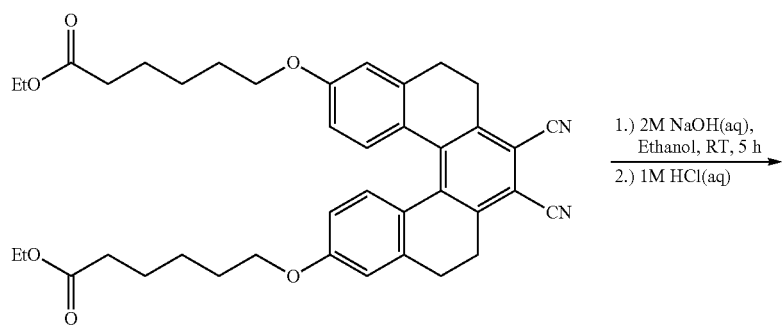

24

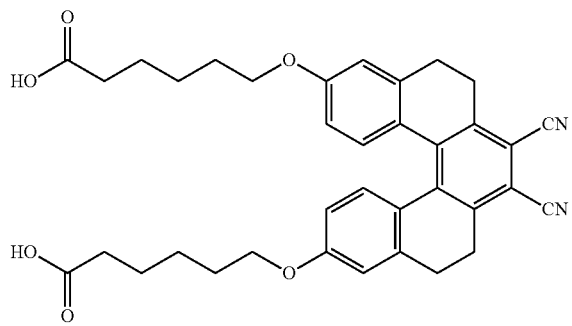

EXAMPLE 4

The synthesis of 6-((3,4-dicyano-8-hydroxydibenzo[c,g]phenanthren-13-yl)oxy)hexanoic acid or compound 4

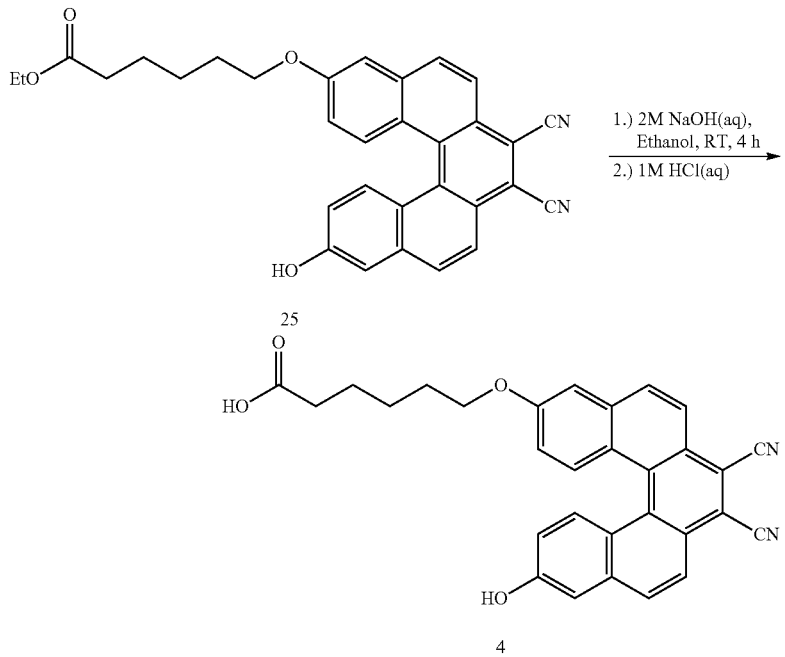

Step a)

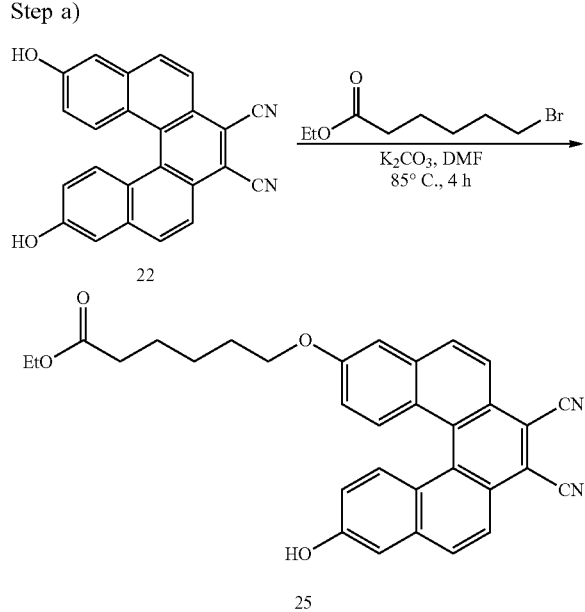

A mixture of 8,13-dihydroxy-dibenzo[c,g]phenanthrene-3,4-dicarbonitrile, compound 22, (1.16 g, 3.23 mmol), ethyl-6-bromohexanolate (0.73 g, 3.29 mmol), potassium carbonate (K$_2$CO$_3$) (0.68 g, 4.94 mmol) and 90 mL of DMF was stirred and heated at 85° C. under argon atmosphere for 4 h. After cooling to room temperature, the reaction mixture was poured into 800 ml of water with vigorous stirring for 1 h. The aqueous layer was extracted with ethyl acetate. The organic layer was dried with anhydrous Na$_2$SO$_4$ and the solvent was removed to yield the crude product. The crude was purified by column chromatography (SiO$_2$, 25% to 50% EtOAc-Hexane) to give ethyl 6-((3,4-dicyano-13-hydroxydibenzo[c,g]phenanthren-8-yl)oxy)hexanoate or compound 25, (0.64 g, 40% yield) as a brown solid.

Step b)

Ethyl 6-((3,4-dicyano-13-hydroxydibenzo[c,g]phenanthren-8-yl)oxy) hexanoate, compound 25, (0.64 g, 1.32 mmol) in 10 ml of ethanol and 4 ml of 2M NaOH (aq) were mixed and stirred at room temperature under argon atmosphere for 4 h. After ethanol was removed under reduced pressure, the reaction mixture was acidified by adding 1M HCl dropwise until pH equals to 0 and orange solid was precipitated out from the solution. The solid was filtered, washed with water and dried. The corresponding product 6-((3,4-dicyano-13-hydroxydibenzo[c,g]phenanthren-8-yl)oxy)hexanoic acid or compound 4 was obtained as an orange solid (0.54 g, 87% yield).

$^1$H NMR (500 MHz, MeOD-d$_4$): δ 8.11-8.06 (m, 5H), 8.02 (d, J=9.0 Hz, 1H), 7.43 (s, 1H), 7.30 (s, 1H), 6.90 (d, J=8.0 Hz, 1H), 6.84 (d, J=9.0 Hz, 1H), 4.19 (t, J=6.5 Hz, 2H), 2.33 (t, J=7.0 Hz, 2H), 1.90 (quin, J=7.0 Hz, 2H), 1.73 (quin, J=7.0 Hz, 2H), 1.60 (quin, J=7.0 Hz, 2H) ppm.

$^{13}$C NMR (125 MHz, MeOD-d$_4$): δ 160.85, 159.59, 137.36, 137.14, 131.14, 131.75, 131.48, 131.36, 131.23, 131.01, 129.39, 129.16, 125.16, 124.86, 123.36, 123.22, 118.51, 118.25, 117.60, 117.36, 114.12, 113.78, 111.34, 109.06, 69.28, 35.84, 30.04, 26.91, 26.23 ppm.

FT-IR (KBr): ν$_{max}$ 3222, 2922, 2223, 1708, 1614, 1565, 1490, 1354, 1236, 1186, 858, 529 cm$^{-1}$.

EXAMPLE 5

The synthesis of sodium 3-((8-((5-carboxypentyl)oxy)-3,4-dicyanodibenzo[c,g]phenanthren-13-yl)oxy)propane-1-sulfonate or compound 5

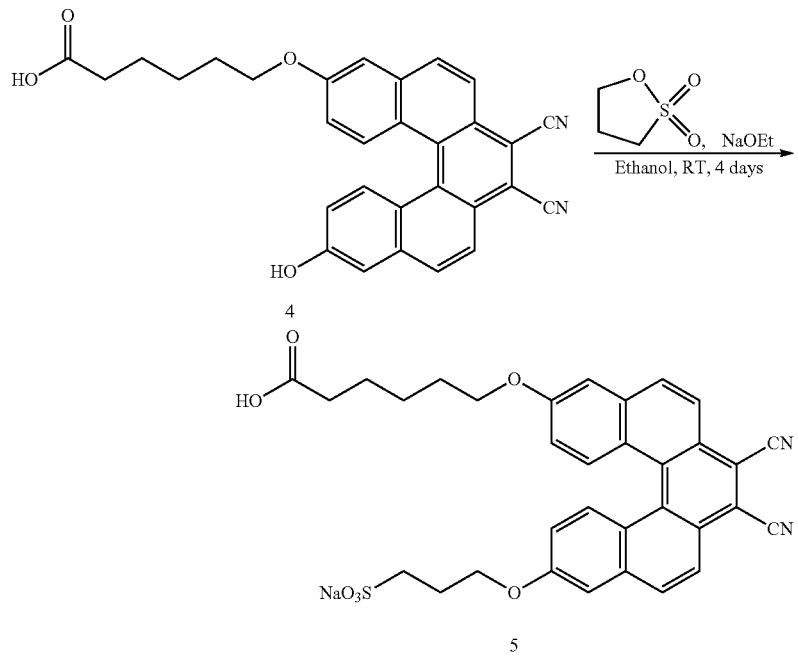

A mixture of 6-((3,4-dicyano-13-hydroxydibenzo[c,g]phenanthren-8-yl)oxy)hexanoic acid or compound 4 (0.70 g, 1.48 mmol) in dry ethanol (45 mL) was stirred until all solids disappeared under argon atmosphere. A mixture of sodium ethoxide (0.15 g, 2.22 mmol) in 10 mL of dry ethanol was added dropwise and stirred for 1 h, causing the yellow solution to turn orange-brown. Then, 1,3 propanesultone (0.19 g, 1.62 mmol) in 5 mL of dry ethanol was added to the mixture. The reaction mixture was stirred at room temperature for 4 days. The reaction was followed by using TLC and precipitation of orange solid. Removing of ethanol by distillation under reduced pressure gave the crude product. The crude product was purified by column chromatography using reversed phased silica gel (50% MeOH:$H_2O$) to give pure product, sodium 3-((8-((5-carboxypentyl)oxy)-3,4-dicyanodibenzo[c,g] phenanthren-13-yl)oxy) propane-1-sulfonate or compound 5, as yellow-green solid (0.12 g, 27% yield).

$^1$H NMR (500 MHz, MeOD-$d_4$): δ 8.15-8.19 (m, 5H), 7.49 (d, J=2.3 Hz, 2H), 6.95-6.70 (m, 3H), 4.33 (t, J=6.5 Hz, 2H), 4.18 (t, J=6.5 Hz, 2H), 3.04 (t, J=7.5 Hz, 2H), 2.34 (quin, J=7.0 Hz, 2H), 2.20 (t, J=7.5 Hz, 2H), 1.89 (quin, J=8 Hz, 2H), 1.70 (quin, J=7.5 Hz, 2H), 1.57 (quin, J=8 Hz, 2H) ppm.

$^{13}$C NMR (125 MHz, MeOD-$d_4$): δ 161.09, 160.79, 137.28, 131.61, 130.92, 129.48, 128.63, 125.85, 125.70, 123.52, 123.40, 123.36, 118.79, 116.56, 109.30, 109.13, 69.46, 68.16, 39.14, 30.75, 30.18, 27.49, 27.23, 26.27 ppm FT-IR (KBr): $v_{max}$ 3435, 2928, 2224, 1614, 1565, 1450, 1408, 1358, 1192, 1051, 861, 796, 671, 537, 459 cm$^{-1}$.

EXAMPLE 6

The synthesis of 6,6'-((3,4-dicyanodibenzo[c,g]phenanthrene-8,13-diyl)bis(oxy)) dihexanoic acid or compound 6

Step a)

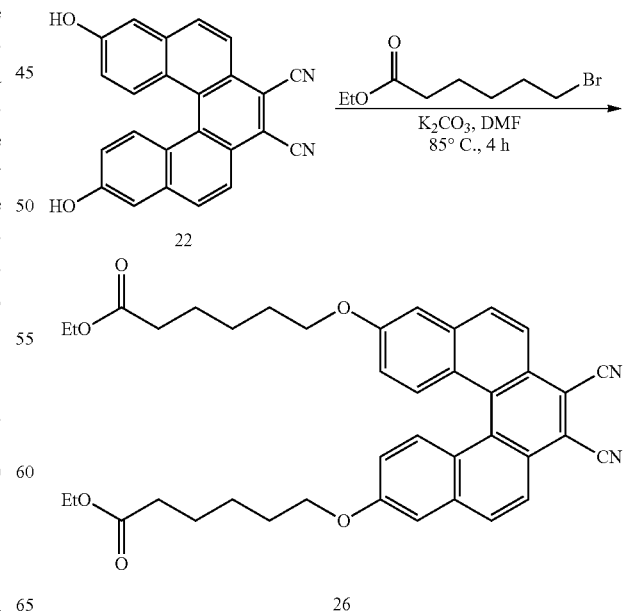

A mixture of 8,13-dihydroxy-dibenzo[c,g]phenanthrene-3,4-dicarbonitrile, compound 22, (1.16 g, 3.23 mmol), ethyl-6-bromohexanolate (0.73 g, 3.29 mmol), potassium carbonate ($K_2CO_3$) (0.68 g, 4.94 mmol) and 90 mL of DMF was stirred and heated at 85° C. under argon atmosphere for 4 h. After cooling to room temperature, the reaction mixture was poured into 800 ml of water with vigorous stirring for 1 h. The aqueous layer was extracted with ethyl acetate. The organic layer was dried with anhydrous $Na_2SO_4$ and the solvent was removed to yield the crude product. The crude was purified by column chromatography ($SiO_2$, 50% EtOAc-Hexane) to give diethyl 6,6'-((3,4-dicyano-dibenzo[c,g]phenanthrene-8,13-diyl)bis(oxy))dihexanoate, compound 26, (0.59 g, 28% yield) as a yellow solid.

Step b)

Diethyl 6,6'-((3,4-dicyano-dibenzo[c,g] phenanthrene-8,13-diyl)bis(oxy)) dihexanoate, compound 26, (0.20 g, 3.30 mmol) in 30 ml of ethanol and 10 ml of 2M NaOH (aq) were mixed and stirred at room temperature under argon for 4 h. After ethanol was removed under reduced pressure, 1M HCl was added dropwise into reaction until pH equals to 0 and orange solid was precipitated out from the solution. The solid was filtered, washed with water and dried. The corresponding product, 6,6'-((3,4-dicyanodibenzo[c,g]phenanthrene-8,13-diyl)bis(oxy)) dihexanoic acid or compound 6 was obtained as orange solid (0.162 g, 83% yield).

$^1$H NMR (500 MHz, MeOD-d$_4$): δ 8.18 (d, J=7.5 Hz, 1H), 8.12 (d, J=2.0 Hz, 1H), 8.07 (d, J=4.0 Hz, 1H), 7.99 (d, J=9.0 Hz, 1H), 7.95 (s, 1H), 7.88 (d, J=8.5 Hz, 1H), 7.33-7.41 (m, 2H), 6.84-6.91 (m, 2H), 4.16 (q, J=6.3 Hz, 4H), 2.33 (q, J=7.0 Hz, 4H), 1.86 (quin, J=6.0 Hz, 4H), 1.70 (quin, J=7.0 Hz, 4H), 1.46 (quin, J=7.0 Hz, 4H) ppm.

$^{13}$C NMR (125 MHz, DMSO-d$_6$): δ 174.63, 170.51, 158.76, 157.29, 135.28, 134.54, 130.44, 129.85, 129.71, 129.42, 128.60, 127.44, 125.62, 124.61, 124.36, 122.47,

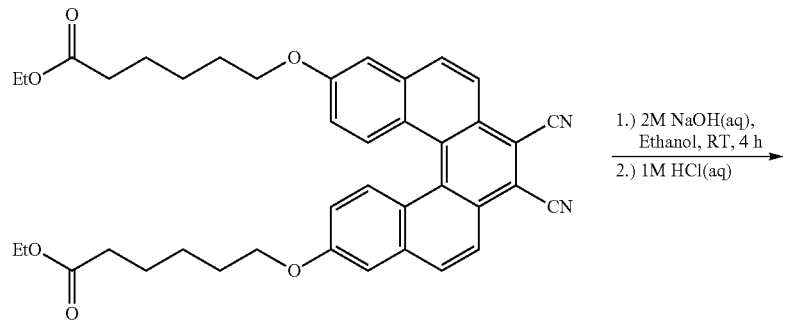

26

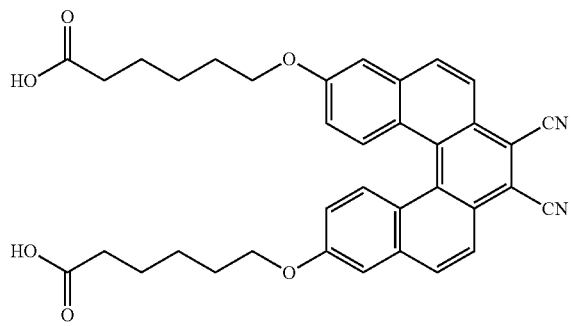

6

122.03, 121.16, 117.34, 116.59, 115.56, 112.41, 108.08, 107.98, 67.52, 33.84, 28.45, 25.24, 24.39 ppm.

FT-IR (KBr): $v_{max}$ 3065, 2936, 2223, 1704, 1615, 1447, 1354, 1280, 1235, 1183, 849, 667, 539 cm$^{-1}$.

EXAMPLE 7

The synthesis of 8-hydroxy-13-(((6-oxohexyl)oxy)-1,2,5,6-tetrahydrodibenzo[c,g] phenanthrene-3,4-dicarbonitrile or compound 7
Step a)

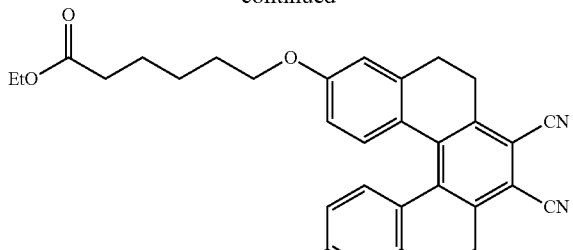

23

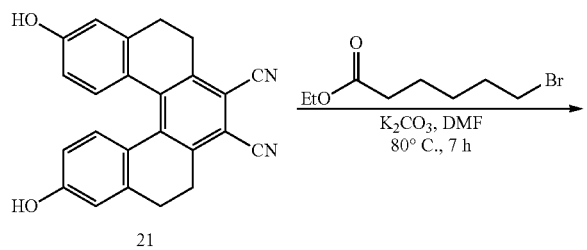

A mixture of 8,13-dihydroxy-1,2,5,6-tetrahydrodibenzo[c,g] phenanthrene-3,4-dicarbo nitrile, compound 21, (2.00 g, 5.50 mmol), ethyl 6-bromohexanoate (1.64 g, 7.35 mmol), potassium carbonate (K$_2$CO$_3$) (1.51 g, 10.95 mmol) and 180 mL of DMF in a 250 mL round-bottom flask were stirred and heated at 80° C. under argon atmosphere for 7 h. After cooling to room temperature, the reaction mixture was dumped into water (1000 mL) with vigorous stirring for 1 h. The aqueous layer was extracted with ethyl acetate (300 mL×2). The organic layer was dried with Na$_2$SO$_4$ and removed to yield a crude product. The crude product was purified by normal phase column chromatography (silica gel, 20% to 50% EtOAc-Hexane) to give pure ethyl 6-((3,4-dicyano-13-hydroxy-1,2,5,6-tetrahydrodibenzo[c,g] phenanthren-8-yl)oxy)hexanoate, compound 23, as yellow solid (1.68 g, 57% yield). This compound was used for the next step.
Step b)

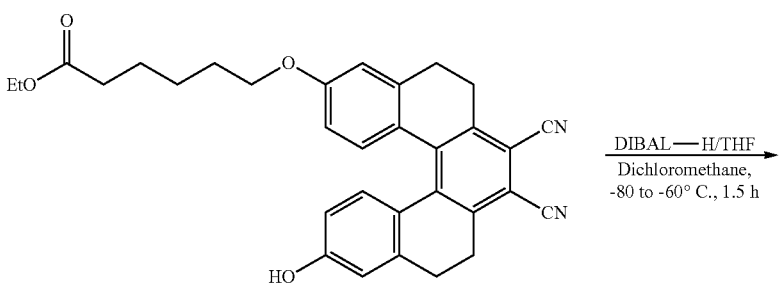

23

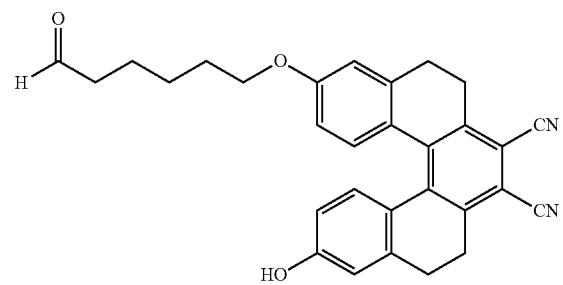

7

Ethyl 6-((3,4-dicyano-13-hydroxy-1,2,5,6-tetrahydrodibenzo[c,g] phenanthren-8-yl)oxy) hexanoate, compound 23, (0.25 g, 0.49 mmole) was dissolved in CH$_2$Cl$_2$ (7 mL) and stirred at −80 to −60° C. under argon for 15 min. Then a solution of 1M DIBAL-H in THF (4 mL) was added. The reaction was controlled temperature at −80 to −60° C. under argon for 1.5 hours. The reaction was added dropwise methanol (10 mL) and water (15 mL) and continued to stir under argon for 30 min. The aqueous layer was extracted with dichloromethane (100 mL×2). The organic layer was dried with anhydrous Na$_2$SO$_4$ and removed under reduced pressure to yield crude product. The crude was purified by column chromatography (30% EtOAc-Hexane to 100% EtOAc) to give 8-hydroxy-13-((6-oxohexyl)oxy)-1,2,5,6-tetrahydrodibenzo[c,g]phenanthrene-3,4-dicarbo nitrile or compound 7 as yellow solid (0.057 g, 25% yield).

$^1$H NMR (500 MHz, CDCl$_3$): δ 9.77 (s, 1H), 7.10 (dd, J=13.0, 8.5 Hz, 2H), 6.76 (dd, J=13.0, 2.0 Hz, 2H), 6.45 (ddd, J=13.0, 8.5, 2.0 Hz, 2H), 5.14 (s, 1H), 4.10-3.90 (m, 2H), 3.32 (d, J=14.7 Hz, 2H), 2.95-2.80 (br s, 4H), 2.70-2.55 (m, 2H), 2.48 (t, J=7.5 Hz, 2H), 1.85-1.75 (m, 2H), 1.75-1.62 (m, 2H), 1.55-1.45 (m, 2H) ppm.

$^{13}$C NMR (125 MHz, CDCl$_3$): δ 202.52, 159.56, 156.23, 143.57, 143.53, 140.97, 140.65, 137.19, 137.02, 131.38, 131.15, 125.52, 125.19, 14.39, 113.51, 113.24, 112.56, 67.59, 43.77, 28.96, 28.81, 28.60, 28.47, 28.42, 25.67, 21.74 ppm.

FT-IR (KBr): ν$_{max}$ 3368, 2943, 2861, 2723, 2223, 1713, 1605, 1577, 1545, 1498, 1273, 1242, 1091, 1019, 819, 609 cm$^{-1}$.

EXAMPLE 8

The synthesis of 8,13-bis((6-oxohexyl)oxy)-1,2,5,6-tetrahydrodibenzo[c,g]phenanthrene-3,4-dicarbonitrile or compound 8

Step a)

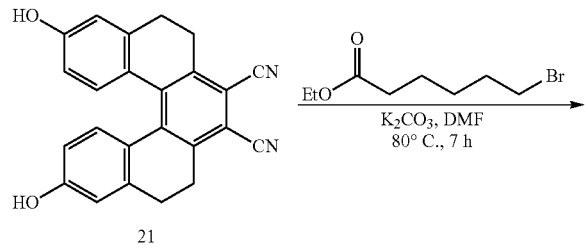

A mixture of 8,13-dihydroxy-1,2,5,6-tetrahydrodibenzo[c,g]phenanthrene-3,4-dicarbo nitrile, compound 21, (0.50 g, 1.37 mmol), ethyl-4-bromobutyrate (0.67 g, 3.00 mmol), potassium carbonate (K$_2$CO$_3$) (0.57 g, 4.13 mmol) and 15 mL of DMF were stirred and heated at 80° C. under argon atmosphere for 7 h. After cooling to room temperature, the reaction mixture was dumped into water (600 mL) with vigorous stirring for 1 h. The aqueous layer was extracted with ethyl acetate (200 mL×2). The organic layer was dried with Na$_2$SO$_4$ and removed to yield a crude product. The crude product was purified by normal phase column chromatography (silica gel, 50% EtOAc-Hexane) to give pure diethyl 6,6'-((3,4-dicyano-1,2,5,6-tetrahydrodibenzo [c,g] phenanthrene-8,13-diyl)bis(oxy))dihexanoate, compound 24 as yellow solid (0.82 g, 92% yield).

Step b)

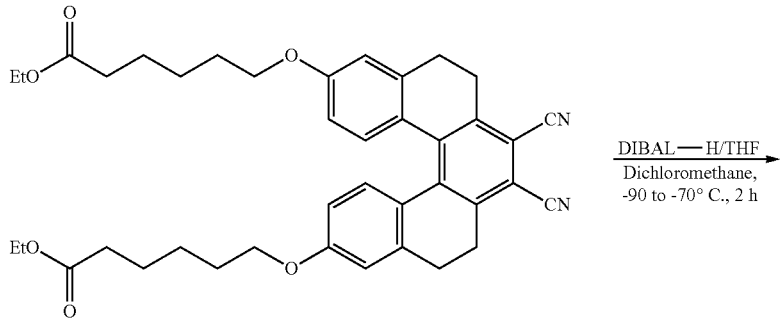

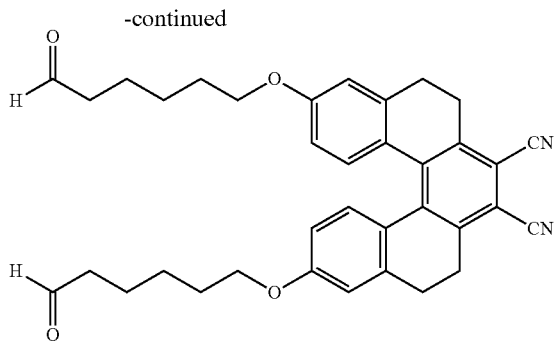

8

Diethyl 6,6'-((3,4-dicyano-1,2,5,6-tetrahydrodibenzo[c,g] phenanthrene-8,13-diyl)bis (oxy))dihexanoate or compound 24 (0.50 g, 0.77 mmole) was dissolved in dichloromethane, (CH$_2$Cl$_2$) (10 mL) and stirred at −90 to −70° C. under argon atmosphere for 15 min. Then 1M of diisobutylaluminum hydride, DIBAL-H, solution in THF (8 mL) was added dropwise into the reaction mixture. The reaction was stirred at −90 to −70° C. under argon atmosphere for 2 hours. The reaction was quenched by adding dropwise methanol (10 mL) and water (20 mL) at −90 to −70° C. and continued stirring for 30 min. The aqueous layer was extracted with CH$_2$Cl$_2$ (50 mL×2). The organic layer was dried with anhydrous Na$_2$SO$_4$. Then the solvent was removed to yield the crude product. The crude was purified by column chromatography (SiO$_2$, 30% EtOAc-Hexane) to give 8,13-bis ((6-oxohexyl)oxy)-1,2,5,6-tetrahydrodibenzo[c,g] phenanthrene-3,4-dicarbo nitrile or compound 8 as yellow solid (0.33 g, 76% yield, mp. 135-139° C.).

$^1$H NMR (500 MHz CDCl$_3$): δ 9.77 (s, 2H), 7.11 (d, J=9.0 Hz, 2H), 6.77 (d, J=1.5 Hz, 2H), 6.47 (dd, J=2.5, 9.0 Hz, 2H), 3.94 (s, 4H), 3.32 (d, J=15.0 Hz, 2H), 2.64 (s, 4H), 2.47 (t, d=7.5 Hz, 2H), 1.90-1.75 (m, 4H), 1.75-1.60 (m, 4H), 1.55-1.45 (m, 4H) ppm.

$^{13}$C NMR (125 MHz, CDCl$_3$): δ 159.52, 143.52, 140.59, 137.10, 131.10, 125.21, 115.57, 113.11, 112.57, 111.40, 67.56, 43.76, 28.97, 28.81, 28.46, 25.66, 21.73 ppm.

FT-1R (KBr): ν$_{max}$ 2942, 2908, 2856, 2722, 2221, 1722, 1606, 1541, 1502, 1274, 1244, 1109, 854, 820, 808 cm$^{-1}$.

EXAMPLE 9

The synthesis of 8((6-hydroxyhexyl)oxy)-13-((6-oxohexyl)oxy)-1,2,5,6-tetrahydro dibenzo[c,g]phenanthrene-3,4-dicarbonitrile or compound 9

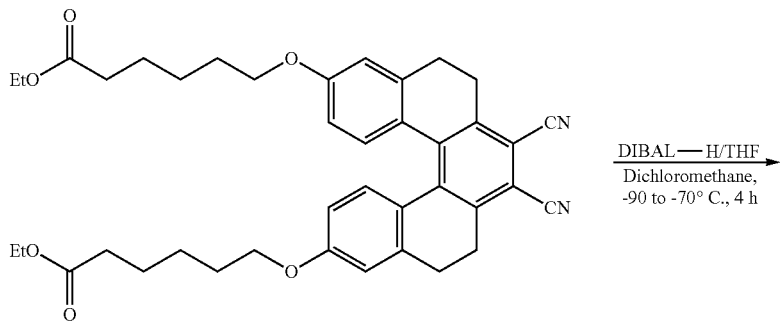

24

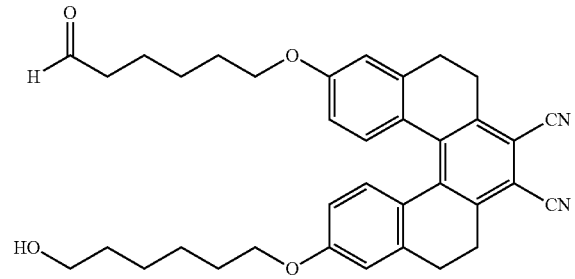

9

Diethyl 6,6'-((3,4-dicyano-1,2,5,6-tetrahydrodibenzo[c,g] phenanthrene-8,13-diyl)bis (oxy))dihexanoate or compound 24 (1.00 g, 1.54 mmole) was dissolved in dichloromethane, (CH$_2$Cl$_2$) (20 mL) and stirred at −90 to −70° C. under argon atmosphere for 15 min. Then 1M of diisobutylaluminum hydride, DIBAL-H, solution in THF (15 mL) was added dropwise into the reaction mixture. The reaction was stirred at −90 to −70° C. under argon atmosphere for 4 hours. The reaction was quenched by adding dropwise methanol (30 mL) and water (30 mL) at −90 to −70° C. and continued stirring for 30 min. The aqueous layer was extracted with CH$_2$Cl$_2$ (200 mL×2). The organic layer was dried with anhydrous Na$_2$SO$_4$. Then the solvent was removed to yield the crude product. The crude was purified by column chromatography (SiO$_2$, 30% EtOAc-Hexane to 100% EtOAc) to give 8-((6-hydroxyhexyl)oxy)-13-((6-oxohexyl)oxy)-1,2,5, 6-tetrahydrodibenzo[c,g]phenanthrene-3,4-dicarbonitrile or compound 9 as yellow solid (0.45 g, 47% yield).

$^1$H NMR (500 MHz, CDCl$_3$): δ 9.80 (s, 1H), 7.12 (dd, J=2.0, 8.5 Hz, 2H), 6.90 (s, 2H), 6.50 (dd, J=3.5, 8.5 Hz, 2H), 3.97 (s, 2H), 3.67 (t, J=6.5 Hz, 2H), 3.33 (d, J=14.0 Hz, 2H), 3.00-2.78 (m, 4H), 2.72-2.53 (m, 2H), 2.50 (t, J=6.5 Hz, 2H), 1.95-1.78 (m, 4H), 1.71 (quin, J=7.5 Hz, 2H), 1.62 (quin, J=7.0 Hz, 2H), 1.60-1.38 (m, 6H) ppm.

$^{13}$C NMR (125 MHz, CDCl$_3$): δ 202.48, 159.61, 159.50, 143.51(2), 140.56(2), 137.13, 137.08, 131.08(2), 125.21, 125.11, 115.56(2), 113.11(2), 112.56, 111.32(2), 67.84, 67.55, 62.79, 43.73, 32.56, 29.13, 28.94, 28.79(2C), 28.45 (2), 25.83(2), 25.49, 21.71 ppm.

FT-IR (KBr): ν$_{max}$ 3390, 2937, 2858, 2222, 1717, 1606, 1542, 1500, 1387, 1272, 1243, 1011, 853, 611 cm$^{-1}$.

EXAMPLE 10

The synthesis of ethyl 4-((3,4-dicyano-13-(4-oxobutoxy)-1,2,5,6-tetrahydrodibenzo [c,g]phenanthren-8-yl)oxy)butanoate or compound 10
Step a)

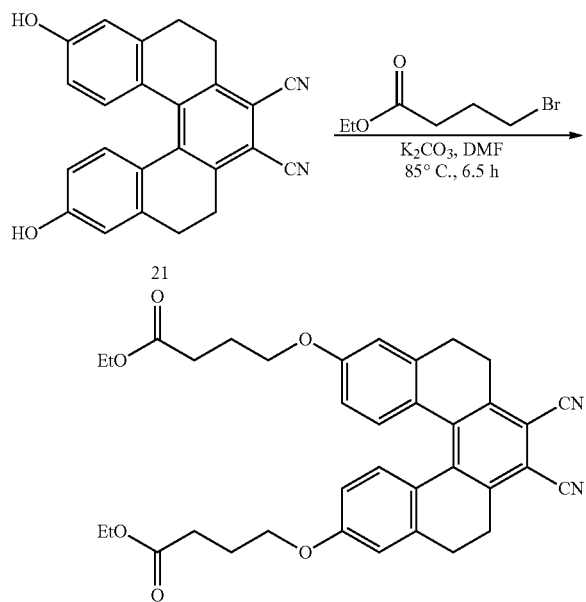

A mixture of 8,13-dihydroxy-1,2,5,6-tetrahydrodibenzo [c,g] phenanthrene-3,4-dicarbo nitrile or compound 21 (1.00 g, 2.75 mmol), ethyl-4-bromobutanoate (2.14 g, 10.99 mmol), potassium carbonate (K$_2$CO$_3$) (1.14 g, 8.25 mmol) and 35 mL of DMF were stirred and heated at 85° C. under argon atmosphere for 6.5 hours. The reaction was cooled to room temperature and dumped into 800 mL of water. The aqueous layer was extracted with EtOAc (250 mL×2). The organic layer was dried with anhydrous Na$_2$SO$_4$ and the solvent was removed to yield the crude product. The crude was purified by column chromatography (SiO$_2$, 40% EtOAc-Hexane) to give diethyl 4,4'-((3,4-dicyano-1,2,5,6-tetrahydrodibenzo[c,g] phenanthrene-8,13-diyl)bis(oxy)) dibutyrate or compound 27 as yellow solid (1.13, 65% yield).
Step b)

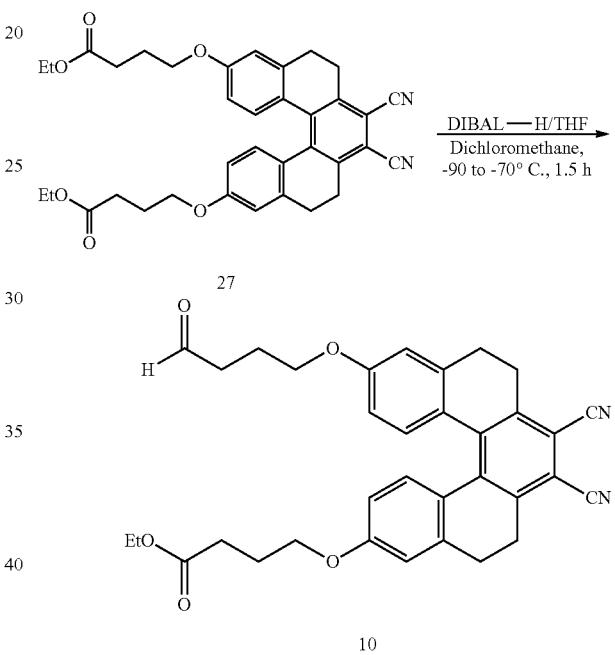

diethyl 4,4'-((3,4-dicyano-1,2,5,6-tetrahydrodibenzo[c,g] phenanthrene-8,13-diyl)bis(oxy)) dibutyrate or compound 27 (0.60 g, 1.04 mmol) was dissolved in CH$_2$Cl$_2$ (25 mL) and stirred at −90 to −70° C. under argon atmosphere for 15 min. 1M DIBAL-H in THF (9 mL) was added to the reaction solution. The reaction was stirred at −90 to −70° C. under argon atmosphere for 1.5 hours. The reaction was quenched by adding dropwise of MeOH (10 mL) and water (15 mL) at −90 to −70° C. under argon for 30 min. The aqueous layer was extracted with CH$_2$Cl$_2$ (100 mL×2). The organic layer was dried with anhydrous Na$_2$SO$_4$ and the solvent was removed to yield the crude product. The crude was purified by column chromatography (SiO$_2$, 30% to 50% EtOAc-Hexane) to give ethyl 4-((3,4-dicyano-13-(4-oxobutoxy)-1, 2,5,6-tetrahydrodibenzo[c,g] phenanthren-8-yl)oxy)butanoate or compound 10 as yellow solid (0.16 g, 29% yield).

$^1$H NMR (500 MHz, CDCl$_3$): δ 9.83 (s, 1H), 7.10 (dd, J=3.5, 8.5 Hz, 2H), 6.78 (s, 2H), 6.47 (t, J=3.5 Hz, 2H), 4.13 (q, J=7.0 Hz, 2H), 4.00 (s, 4H), 3.32 (d, J=14.5 Hz, 2H), 2.92-2.78 (m, 4H), 2.66 (t, J=7.0 Hz, 2H), 2.64-2.52 (br s, 2H), 2.50 (t, J=7.0 Hz, 2H), 2.20-2.05 (m, 4H), 1.25 (t, J=7.0 Hz, 3H) ppm.

$^{13}$C NMR (125 MHz, CDCl$_3$): δ 173.13, 159.37, 159.19, 143.56(2), 140.66(2), 137.13, 137.05, 131.14(2), 125.49, 125.32, 115.55(2), 113.22, 113.17, 112.65, 112.53, 111.52, 111.49, 66.76, 66.68, 60.51, 40.52, 30.72, 28.82(2), 28.47 (2), 24.56, 21.93, 14.23 ppm.

FT-IR (KBr): ν$_{max}$ 3456, 2943, 2909, 2222, 1729, 1606, 1541, 1502, 1272, 1245, 1177, 1032, 856, 611 cm$^{-1}$.

EXAMPLE 11

The synthesis of 8-hydroxy-13-((6-oxohexyl)oxy) dibenzo[c,g]phenanthrene-3,4-dicarbonitrile or compound 11

A mixture of 8,13-dihydroxy-dibenzo[c,g]phenanthrene-3,4-dicarbonitrile, compound 22, (1.16 g, 3.23 mmol), ethyl-6-bromohexanolate (0.73 g, 3.29 mmol), potassium carbonate (K$_2$CO$_3$) (0.68 g, 4.94 mmol) and 90 mL of DMF was stirred and heated at 85° C. under argon atmosphere for 4 h. After cooling to room temperature, the reaction mixture was poured into 800 ml of water with vigorous stirring for 1 h. The aqueous layer was extracted with ethyl acetate. The organic layer was dried with anhydrous Na$_2$SO$_4$ and the solvent was removed to yield the crude product. The crude was purified by column chromatography (SiO$_2$, 25% to 50% EtOAc-Hexane) to give ethyl 6-((3,4-dicyano-13-hydroxydibenzo[c,g]phenanthren-8-yl)oxy)hexanoate or compound 25, (0.64 g, 40% yield) as a brown solid.

Step b)

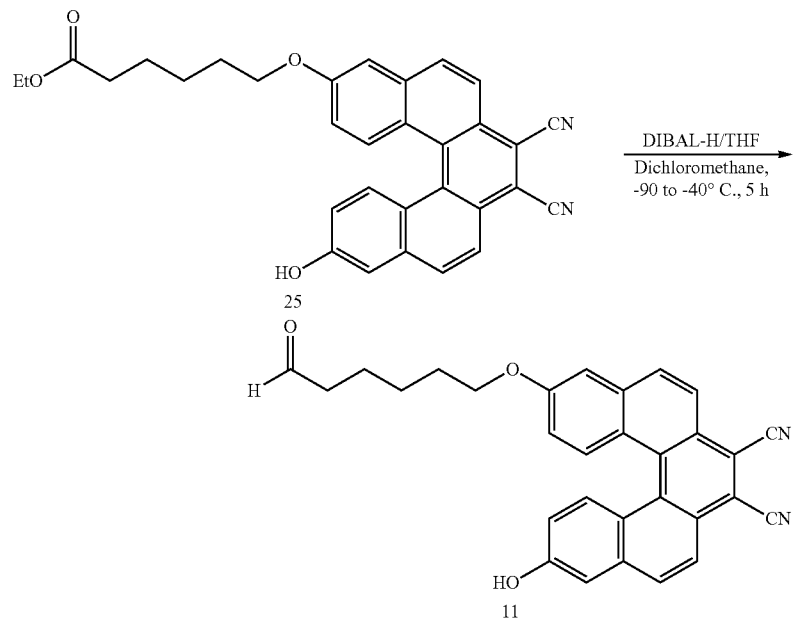

Ethyl 6-43,4-dicyano-13-hydroxydibenzo[c,g]phenanthren-8-yl)oxy) hexanoate, compound 25, (0.30 g, 0.60 mmole) was dissolved in CH$_2$Cl$_2$ (5 mL) and stirred at −90 to −40° C. under argon for 15 min. Then a solution of 1M DIBAL-H in THF (5 mL) was added dropwise. The reaction was controlled temperature at −90 to −40° C. under argon for 5 hours. The reaction was added dropwise methanol (10 mL) and water (15 mL) and continued to stir under argon for 30 min. The aqueous layer was extracted with dichloromethane (50 mL×2). The organic layer was dried with anhydrous Na$_2$SO$_4$ and removed under reduced pressure to yield crude product. The crude was purified by column chromatography (30% EtOAc-Hexane to 100% EtOAc) to give 8-hydroxy-13-((6-oxohexyl)oxy) dibenzo[c,g]phenanthrene-3,4-dicarbonitrile or compound 11 as yellow solid (0.09 g, 36% yield).

$^1$H NMR (500 MHz, CDCl$_3$): δ 9.80 (s, 1H), 8.32-8.17 (m, 3H), 7.98 (dd, J=19.5, 9.0 Hz, 2H), 7.40-7.21 (m, 2H), 7.19-7.11 (m, 1H), 6.91 (t, J=11.0 Hz, 2H), 4.12 (dt, J=9.0, 6.5 Hz, 2H), 2.51 (t, J=7.5 Hz, 2H), 1.90 (quin, J=7.5 Hz, 2H), 1.76 (quin, J=7.0 Hz, 2H), 1.56 (quin, J=7.0 Hz, 2H) ppm.

FT-IR (KBr): ν$_{max}$ 3366, 2927, 2860, 2741, 2223, 1713, 1612, 1565, 1491, 1446, 1354, 1277, 1235, 1179, 1013, 850, 828, 669, 529 cm$^{-1}$.

Step a.)

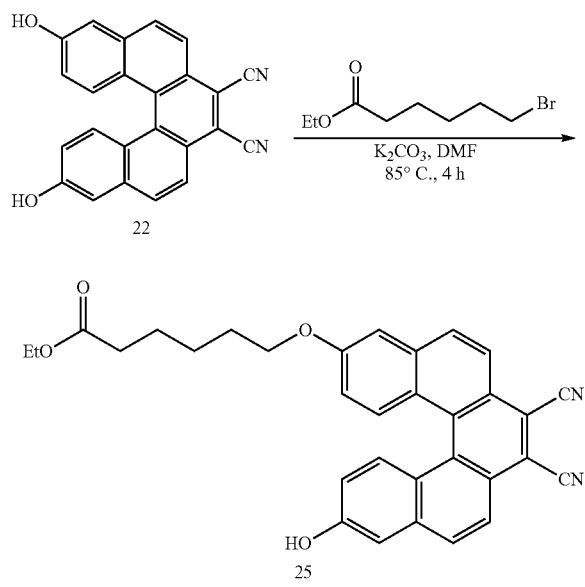

EXAMPLE 12

The synthesis of 8,13-bis((6-oxohexyl)oxy)dibenzo[c,g]phenanthrene-3,4-dicarbonitrile or compound 12

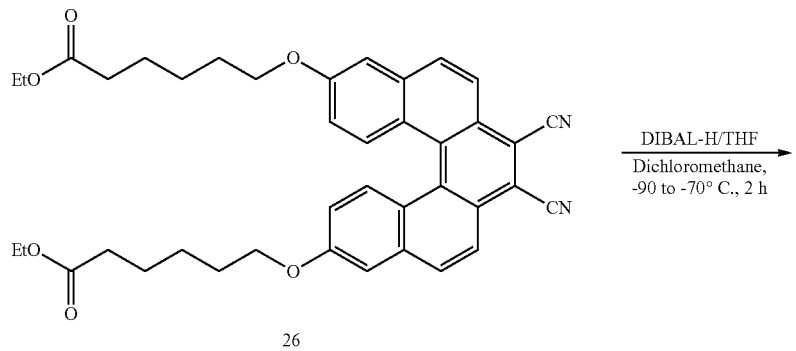

26

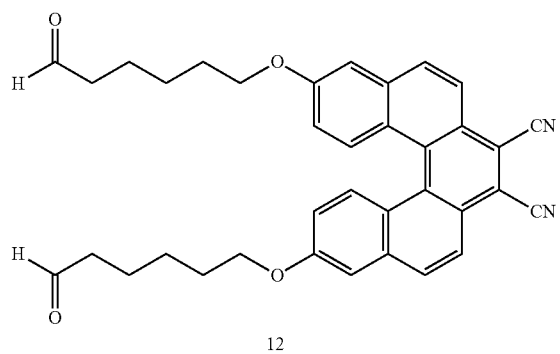

12

Diethyl 6,6'-((3,4-dicyano-dibenzo[c,g] phenanthrene-8,13-diyl)bis(oxy)) dihexanoate, compound 26, (0.25 g, 0.39 mmole) was dissolved in $CH_2Cl_2$ (7 mL) and stirred at −90 to −70° C. under argon for 10 min. Then a solution of 1M DIBAL-H in THF (5 mL) was added dropwise. The reaction was controlled temperature at −90 to −70° C. under argon for 2 hours. The reaction was added dropwise methanol (10 mL) and water (10 mL) and continued to stir under argon for 30 min. The aqueous layer was extracted with dichloromethane (50 mL×2). The organic layer was dried with anhydrous $Na_2SO_4$ and removed under reduced pressure to yield crude product. The crude was purified by column chromatography (30% EtOAc-Hexane) to give 8,13-bis((6-oxohexyl)oxy)dibenzo[c,g]phenanthrene-3,4-dicarbonitrile or compound 12 as yellow solid (0.06 g, 26% yield).

$^1$H NMR (500 MHz, $CDCl_3$): δ 9.70 (s, 2H), 7.25-7.10 (m, 3H), 6.75 (d, J=2.0 Hz, 2H), 6.65-6.50 (m, 1H), 6.52 (dd, J=9.0, 2.0 Hz, 2H), 6.44 (t, J=10.5 Hz, 2H), 3.96 (s, 4H), 2.49 (t, d=7.5 Hz, 4H), 1.90-1.70 (m, 4H), 1.75-1.65 (m, 4H), 1.55-1.40 (m, 4H) ppm.

EXAMPLE 13

The synthesis of sodium 3,3'-((2-(3-carboxypropyl)-1,3-dioxo-4,5,14,15-tetrahydro-1H-dinaphtho[2,1-e:1',2'-g]isoindole-7,12-diyl)bis(oxy))bis(propane-1-sulfonate) or compound 13

Step a)

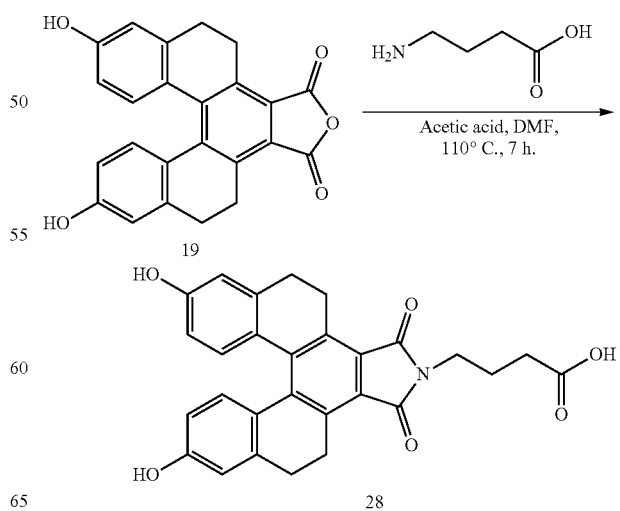

A mixture of 7,12-dihydroxy-4,5,14,15-tetrahydronaphtho[2',1':3,4] phenanthro[1,2-c] furan-1,3-dione, compound 19, (1.00 g, 2.6 mmol), γ-aminobutyric acid (0.04 g, 3.9 mmol), 4 mL of acetic acid and 30 mL of DMF was stirred under argon atmosphere and heated at 110° C. for 7 h. After cooling to room temperature, the reaction mixture was dumped into water (500 mL) with vigorous stirring for 1 h. The yellow solid was collected by vacuum filtration, washed with 100 mL of water, and 50 mL of $CH_2Cl_2$-Hexane (1:1) mixture to give pure product of 4-(7,12-dihydroxy-1,3-dioxo-1,3,4,5,14,15-hexahydro-2H-dinaphtho[2,1-e:1',2'-g]isoindol-2-yl) butanoic acid or compound 28 as a yellow solid (1.17 g, 96% yield).
Step b)

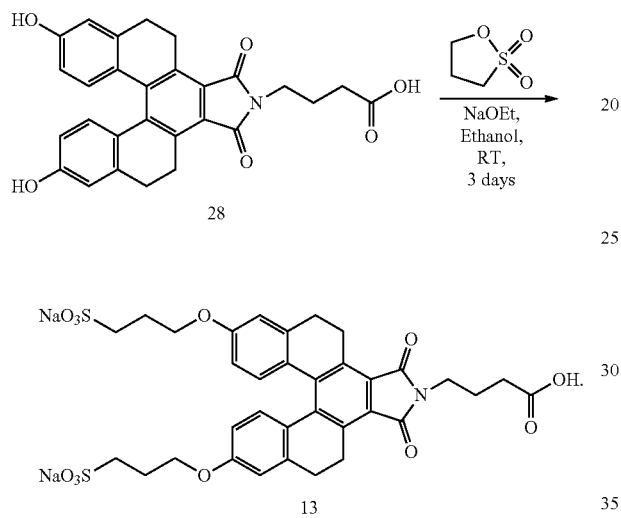

A mixture of 4-(7,12-dihydroxy-1,3-dioxo-1,3,4,5,14,15-hexahydro-2H-dinaphtho[2,1-e:1',2'-g]isoindol-2-yl)butanoic acid or compound 28 (0.20 g, 0.43 mmol) in dry ethanol (10 mL) was stirred until all solids disappeared under argon atmosphere. A mixture of sodium ethoxide (0.09 g, 1.28 mmol) in 5 mL of dry ethanol was added dropwise and stirred for 1 h, causing the yellow solution turn to orange-brown. Then, 1,3 propanesultone (0.11 g, 0.94 mmol) in 5 mL of dry ethanol was added to the mixture. The reaction mixture was stirred for 3 days. The reaction was followed by using TLC and precipitation of orange solid. The crude solid was collected by vacuum filtration and washed with dichloromethane. The crude product was dried in vacuum. The crude product was purified by column chromatography using reversed phased silica gel (1:1, MeOH:$H_2O$) to give pure product of 3,3'-((2-(3-carboxypropyl)-1,3-dioxo-4,5,14, 15-tetrahydro-1H-dinaphtho[2,1-e:1',2'-g]isoindole-7,12-diyl)bis(oxy))bis(propane-1-sulfonate) or compound 13 as yellow-orange solid (0.07 g, 21% yield).
$^1$H NMR (500 MHz, DMSO-$d_6$): δ 7.01 (d, 2H), 6.89 (s, 2H), 6.54 (d, 2H), 4.02 (s, 4H), 3.90 (d, 2H), 2.82 (d, 4H), 2.53 (s, 6H), 2.33 (d, 2H), 1.96 (s, 4H), 1.86 (s, 2H), 1.69 (d, 2H), 1.19 (s, 1H) ppm.
FT-IR (KBr): 3448, 1754, 1695, 1597, 1573, 1392, 1181, 1112, 1046, 795, 615, 530 cm$^{-1}$.

EXAMPLE 14

The synthesis of sodium 3-((1,3-dioxo-12-((6-oxohexyl)oxy)-2-phenyl-4,5,14, 15-tetrahydro-1H-dinaphtho[2,1-e:1',2'-g]isoindol-7-yl)oxy)propane-1-sulfonate or compound 14
Step a.)

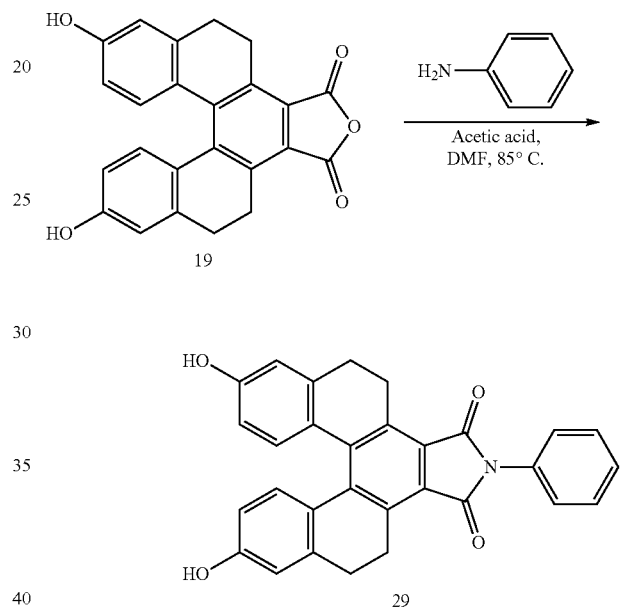

A mixture of 7,12-dihydroxy-4,5,14,15-tetrahydronaphtho[2',1':3,4] phenanthro[1,2-c] furan-1,3-dione, compound 19, (3.00 g, 7.81 mmol), aniline (1.09 g, 11.71 mmol), 10 mL of acetic acid and 60 mL of DMF were stirred and heated at 85° C. under argon atmosphere for 5 hours. After cooling to room temperature, the reaction mixture was dumped into water (800 mL) with vigorous stirring for 1 hour. The yellow solids were collected by vacuum filtration, washed with 500 mL of water, and 100 mL of mixed solvent $CH_2Cl_2$-Hexane (1:1) to give pure compound 29 as a yellow solid (3.19 g, 89% yield).
Step b)

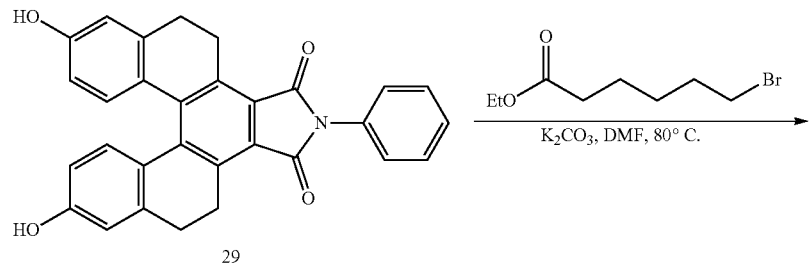

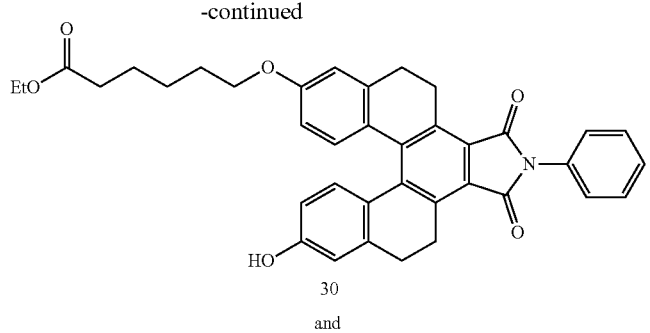

30 and

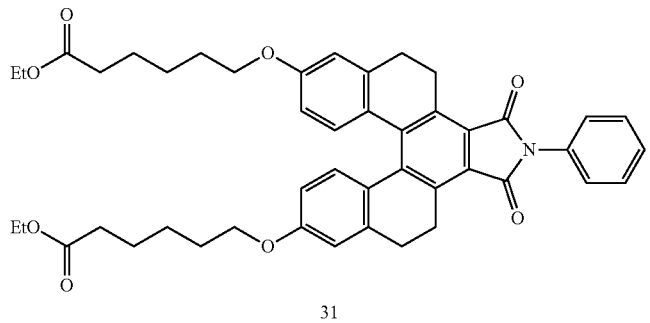

31

A mixture of compound 29 (3.12 g, 6.80 mmol), ethyl-6-bromohexanoate (1.01 g., 4.53 mmol), potassium carbonate ($K_2CO_3$) (0.94 g, 6.80 mmol) and 140 mL of DMF were stirred and heated at 80° C. under argon atmosphere for 5 hours. The reaction was cooled to room temperature and dumbed into 800 mL of water. The aqueous layer was extracted with EtOAc (200 mL×2). The organic layer was dried with anhydrous $Na_2SO_4$ and removed to yield crude product. The crude was purified by column chromatography ($SiO_2$, 25% to 80% EtOAc-Hexane) to give compound 30 (1.49 g, 55% yield) and compound 31 (0.40 g, 24% yield) as yellow-orange solid.

Step c.)

A mixture of compound 30 (1.11 g, 0.27 mmol) in dry ethanol (100 mL) was stirred until all solids disappeared under argon. A mixture of sodium ethoxide, NaOEt, (0.14 g, 2.03 mmol) in 5 mL of dry ethanol was added dropwise and stirred for 1 h, causing the orange solution to turn orange-brown. Then, 1,3 propanesultone (0.14 g, 2.03 mmol) in 5 mL of dry ethanol was added to the mixture. The reaction was stirred for 4 days (followed by TLC) until an orange product was precipitated out from the solution. Ethanol was removed under reduced pressure. The crude product was purified by chromatography (revered-phase $SiO_2$, 25% to 50% $EtOH:H_2O$) to give compound 32 (1.03 g, 75% yield) as yellow solid.

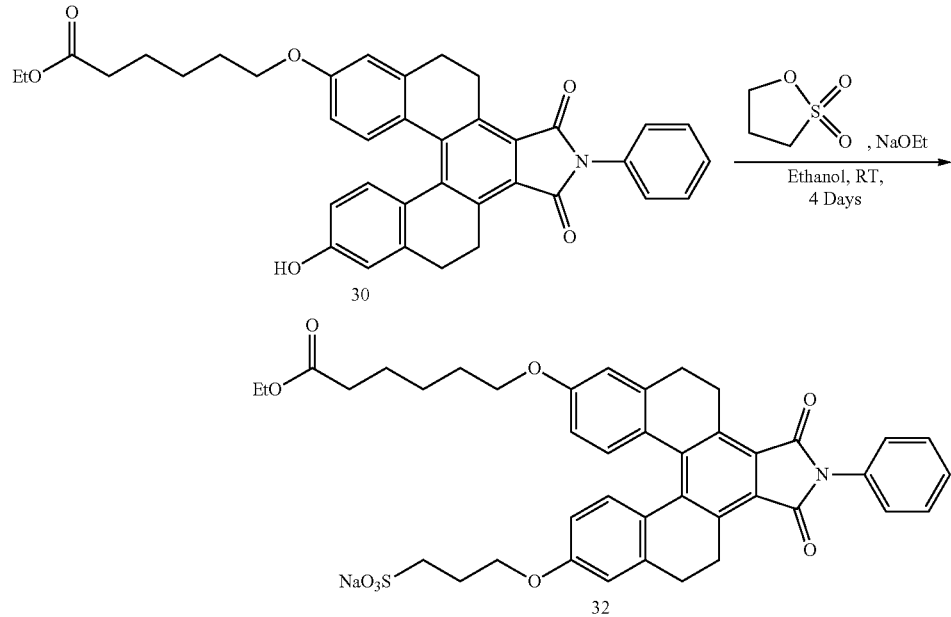

Step d)

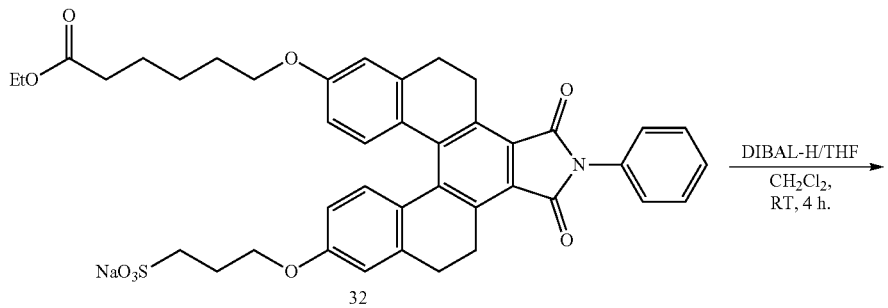

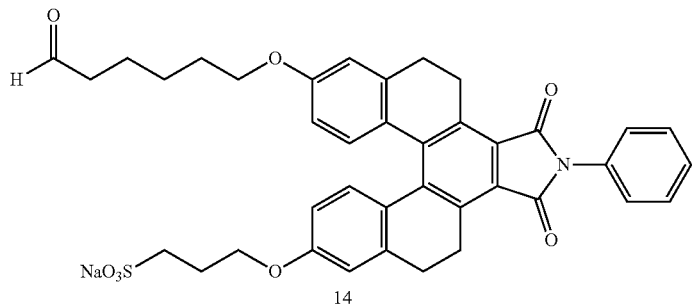

The compound 32 (0.15 g, 0.20 mmol) was dissolved in CH$_2$Cl$_2$ (6 mL) and stirred at room temperature under argon atmosphere for 15 minutes. Then 1M DIBAL in THF (0.5 mL) was added dropwise. The reaction was stirred at room temperature under argon atmosphere for 4 hours. The reaction was added methanol (6 mL) and water (10 mL) and stirred under argon atmosphere for 30 minutes. The solvent, then, was removed under reduced pressure. The crude product was purified by Revered-phase column chromatography (SiO$_2$, EtOH:H$_2$O, 1:1) to give sodium 3-((1,3-dioxo-12-((6-oxohexyl)oxy)-2-phenyl-4,5,14,15-tetrahydro-1H-dinaphtho[2,1-e:1',2'-g]isoindol-7-yl)oxy)propane-1-sulfonate or compound 14 as a yellow solid (71.00 mg, 50% yield).

$^1$H NMR (500 MHz, DMSO-d$_6$): δ 7.49 (t, J=7.5, 2H), 7.39 (d, J=10.5, 3H), 7.05 (d, J=6.5, 2H), 6.91 (s, 2H), 6.55 (t, J=10.5, 2H), 4.12-4.00 (m, 2H), 4.00-3.88 (m, 4H), 2.98-2.70 (m, 4H), 2.52 (t, J=7.5, 2H), 2.45-2.30 (m, 2H), 1.96 (quin, J=7.0, 2H), 1.67 (quin, J=7.0, 2H), 1.48-1.28 (m, 6H) ppm.

$^{13}$C NMR (125 MHz, MeOD-d$_4$): δ 167.29, 158.59, 140.82, 137.59, 137.45, 132.12, 130.74, 130.68, 128.77, 127.93, 127.67, 125.69, 124.75, 113.02, 112.95, 112.49, 112.38, 67.37, 66.63, 60.62, 47.81, 32.46, 28.76, 28.12, 25.42, 25.32, 25.26, 23.80 ppm.

FT-IR (KBr): ν$_{max}$ 3433, 2933, 2855, 1703, 1602, 1501, 1373, 1266, 1207, 1177, 1106, 1043, 761, 624 cm$^{-1}$.

EXAMPLE 15

The synthesis of 6-((12-hydroxy-1,3-dioxo-2-phenyl-4,5,14,15-hexahydro-1H-dinaphtho [2,1-e:1',2'-g]isoindol-7-yl)oxy)hexanal or compound 15

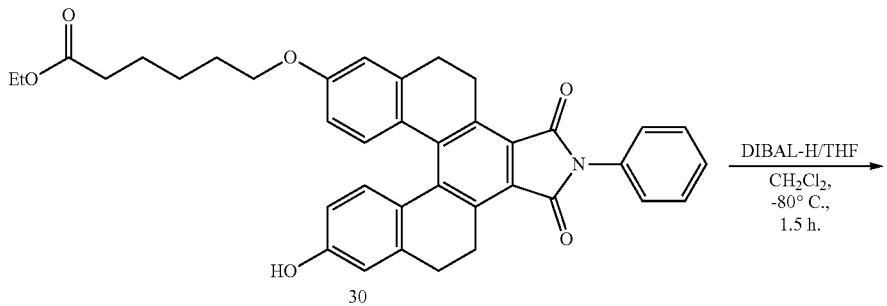

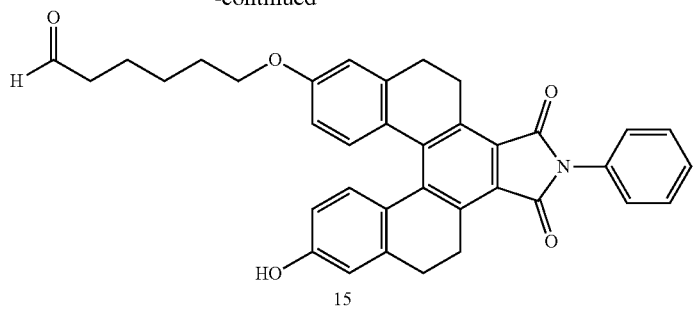

The compound 30 (0.07 g, 0.16 mmol) was dissolved in CH$_2$Cl$_2$ (6 mL) and stirred at −80° C. under argon atmosphere for 10 minutes. Then 1M DIBAL in THF (1.0 mL) was added dropwise. The reaction was stirred at −80° C. under argon atmosphere for 1.5 hours. The reaction was added methanol (20 mL) and water (10 mL) and stirred under argon atmosphere for 30 minutes. The solvent, then, was removed under reduced pressure. The crude product was purified by column chromatography (SiO$_2$, 20% to 50% EtOAc:Hexane) to give 6-((12-hydroxy-1,3-dioxo-2-phenyl-4,5,14,15-hexahydro-1H-dinaphtho[2,1-e:1′,2′-g]isoindol-7-yl)oxy)hexanal or compound 15 as a yellowish brown solid (27 mg, 43% yield).

$^1$H NMR (500 MHz, CDCl$_3$): δ 7.56-7.45 (m, 2H), 7.43-7.31 (m, 3H), 7.13 (dd, J=18.0, 7.5 Hz, 2H), 6.78 (d, J=18.0 Hz, 2H), 6.46 (dd, J=18.0, 7.5 Hz, 2H), 5.18 (s, 1H), 4.12-4.00 (m, 2H), 3.96 (s, 2H), 2.98-2.70 (br s, 4H), 2.60-2.40 (m, 2H), 1.71 (quin, J=7.0 Hz, 2H), 1.50 (quin, J=7.0 Hz, 2H), 1.23 (quin, J=7.0 Hz, 2H) ppm.

EXAMPLE 16

The synthesis of 6,6′-((1,3-dioxo-2-phenyl-2,3,4,5,14,15-hexahydro-1H-dinaphtho[2,1-e:1′,2′-g]isoindole-7,12-diyl)bis(oxy))dihexanal or compound 16

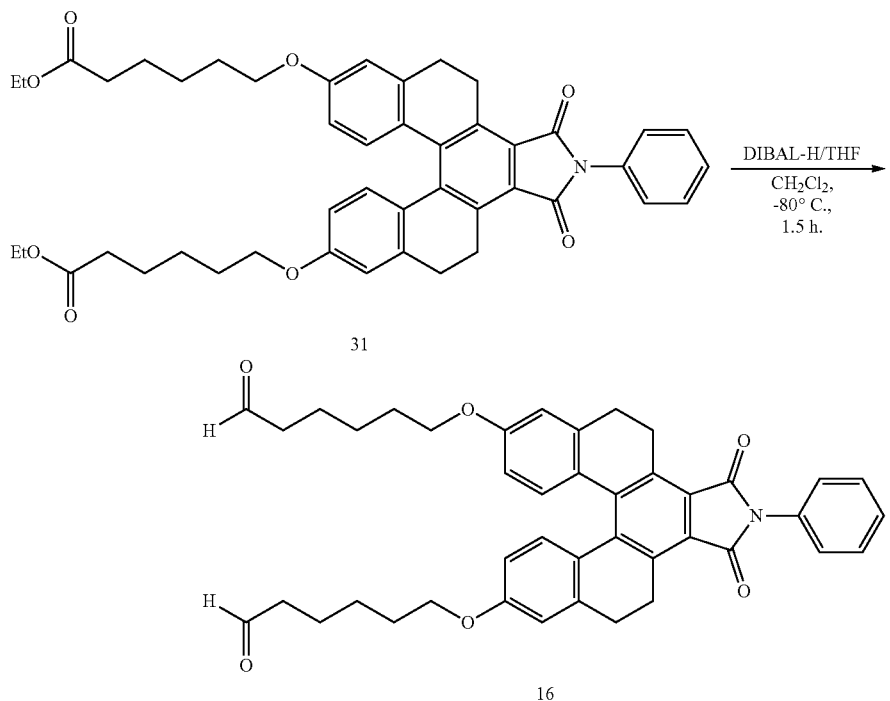

The compound 31 (0.23 g, 0.31 mmol) was dissolved in CH$_2$Cl$_2$ (10 mL) and stirred at −80° C. under argon atmosphere for 10 minutes. Then 1M DIBAL in THF (6.0 mL) was added dropwise. The reaction was stirred at −80° C. under argon atmosphere for 1.5 hours. The reaction was added methanol (20 mL) and water (10 mL) and stirred under argon atmosphere for 30 minutes. The solvent, then, was removed under reduced pressure. The crude product was purified by column chromatography (SiO$_2$, 20% to 50% EtOAc:Hexane) to give 6,6′-((1,3-dioxo-2-phenyl-2,3,4,5,14,15-hexahydro-1H-dinaphtho[2,1-e:1′,2′-g] isoindole-7,12-diyl)bis(oxy))dihexanal or compound 16 as a yellowish brown solid (0.15 g, 72% yield).

¹H NMR (500 MHz, CDCl₃): δ 9.78 (s, 2H), 7.50 (t, J=7.5 Hz, 2H), 7.45-7.32 (m, 3H), 7.15 (d, J=8.5 Hz, 2H), 6.80 (s, 2H), 6.48 (dd, J=8.5, 2.0 Hz, 2H), 4.20-4.05 (br s, 2H), 3.96 (s, 4H), 2.85 (s, 4H), 2.60-2.50 (br s, 2H), 2.47 (t, J=6.0 Hz, 4H), 1.80 (t, J=1.5 Hz, 4H), 1.71 (quin, J=7.5 Hz, 2H), 1.51 (quin, J=7.5 Hz, 2H), 1.24 (quin, J=7.5 Hz, 2H) ppm.

¹³C NMR (125 MHz, CDCl₃): δ 202.45, 167.99, 158.91, 140.99, 138.41, 132.02, 131.31, 128.96, 127.83, 126.88, 126.44, 124.89, 112.99, 112.28, 67.48, 43.79, 29.04, 25.71, 24.25, 21.78 ppm.

FT-IR (KBr): $v_{max}$ 2942, 2842, 2867, 2717, 1761, 1704, 1603, 1501, 1466, 1378, 1264, 1261, 1177, 1103, 1027, 832, 696, 625 cm⁻¹.

EXAMPLE 17

The synthesis of ethyl 6-((1,3-dioxo-12-((6-oxohexyl)oxy)-2-phenyl-4,5,14,15-tetrahydro-1H-dinaphtho[2,1-e:1',2'-g]isoindol-7-yl)oxy)hexanoate or compound 17

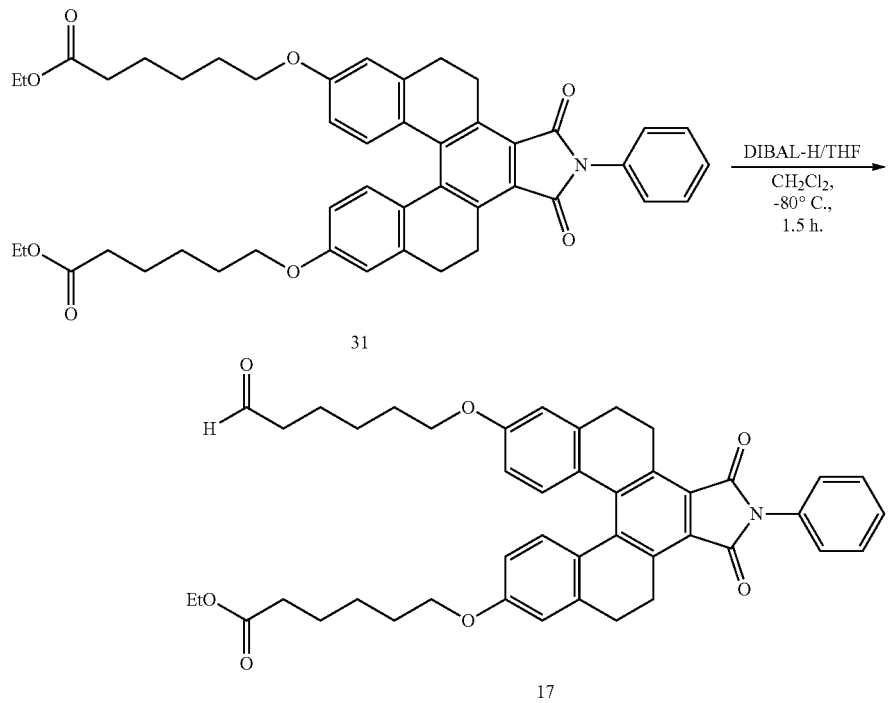

The compound 31 (0.17 g, 0.23 mmol) was dissolved in CH₂Cl₂ (10 mL) and stirred at −80 °C. under argon atmosphere for 10 minutes. Then 1M DIBAL in THF (3.0 mL) was added dropwise. The reaction was stirred at −80° C. under argon atmosphere for 1.5 hours. The reaction was added methanol (20 mL) and water (10 mL) and stirred under argon atmosphere for 30 minutes. The solvent, then, was removed under reduced pressure. The crude product was purified by column chromatography (SiO₂, 20% to 50% EtOAc:Hexane) to give ethyl 6-((1,3-dioxo-12-((6-oxohexyl)oxy)-2-phenyl-4,5,14,15-tetraahydro-1H-dinaphtho[2,1-e:1',2'-g]isoindol-7-yl) oxy)hexanoate or compound 17 as a yellowish brown solid (0.06 g, 35% yield).

¹H NMR (500 MHz, CDCl₃): δ 7.53-7.44 (m, 3H), 7.42-7.35 (m, 2H), 7.15 (d, J=8.5 Hz, 2H), 6.80 (s, 2H), 6.48 (d, J=8.5 Hz, 2H), 4.11 (q, J=7.0 Hz, 2H), 3.95 (s, 4H), 2.84 (s, 4H), 2.60-2.48 (br s, 2H), 2.32 (t, J=7.5 Hz, 4H), 1.79 (quin, J=7.5 Hz, 4H), 1.70 (quin, J=7.5 Hz, 4H), 1.61 (s, 2H), 1.51 (quin, J=7.5 Hz, 4H), 1.24 (quin, J=7.0 Hz, 2H) ppm.

¹³C NMR (125 MHz, CDCl₃): δ 202.47, 168.01, 158.96, 158.91, 140.98, 138.42, 132.03, 130.07, 126.45, 126.39, 124.87, 122.21, 113.00, 112.31, 67.57, 67.49, 60.28, 43.80, 34.24, 29.05, 28.95, 25.72, 25.66, 24.47, 24.26, 21.79, 14.25 ppm.

FT-IR (KBr): $v_{max}$ 2940, 2866, 1763, 1733, 1704, 1603, 1591, 1500, 1466, 1382, 1276, 1264, 1240, 1178, 1103, 1029, 845, 826, 625 cm⁻¹.

EXAMPLE 18

The synthesis of 6-((12-hydroxy-1,3-dioxo-2-phenyl-1H-dinaphtho[2,1-e:1',2'-g]iso indol-7-yl)oxy)hexanal or compound 18

Step a)

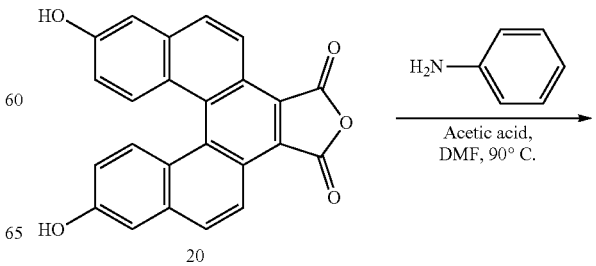

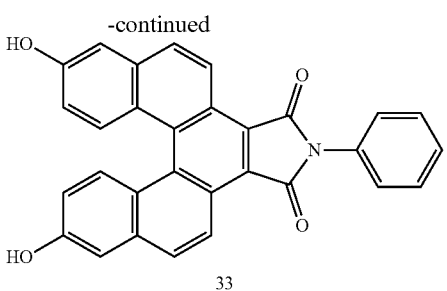

33

A mixture of 7,12-dihydroxytetrahydronaphtho[2',1':3,4]phenanthro[1,2-c]furan-1,3-dione, compound 20, (1.00 g, 2.66 mmol), aniline (0.50 g, 5.32 mmol), 3 mL of acetic acid and 30 mL of DMF was stirred and heated at 90° C. under argon atmosphere for 8 hours 8. After cooling to room temperature, the reaction mixture was dumped into water (500 mL) with vigorous stirring for 1 hour. The yellow solids were collected by vacuum filtration, washed with 250 mL of water, and 100 mL of mixed solvent $CH_2Cl_2$-Hexane (1:1) to give pure compound 33 as a yellow solid (1.15 g, 96% yield) which will be used for the next step.

Step b)

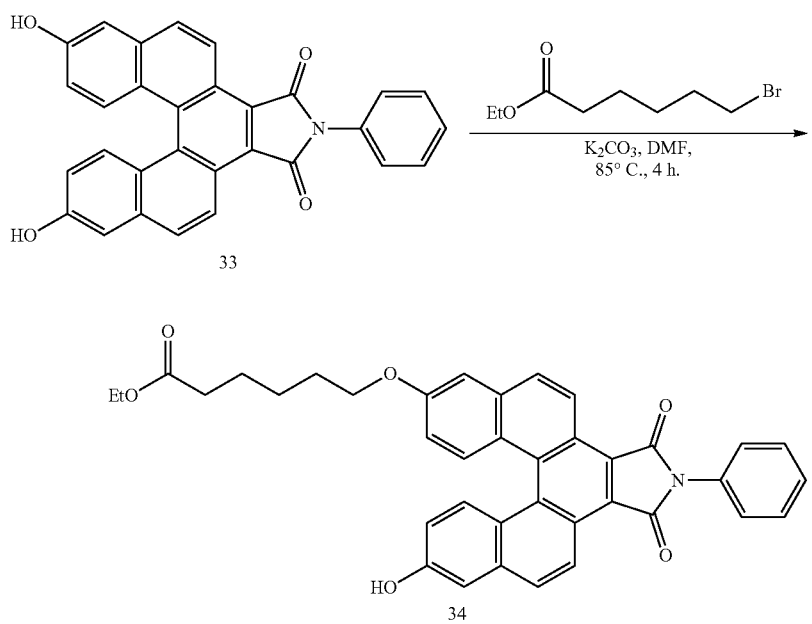

A mixture of compound 33 (0.42 g, 0.92 mmol), ethyl-6-bromohexanoate (0.23 g., 1.05 mmol), potassium carbonate ($K_2CO_3$) (0.17 g, 1.26 mmol) and 40 mL of DMF was stirred and heated at 85° C. under argon atmosphere for 4 hours. The reaction was cooled to room temperature and dumbed into 500 mL of water. The aqueous layer was extracted with EtOAc (200 mL×2). The organic layer was dried with anhydrous $Na_2SO_4$ and removed to yield crude product. The crude was purified by column chromatography ($SiO_2$, 25% to 80% EtOAc-Hexane) to give compound 34 (0.16 g, 29% yield) as yellow-orange solid which will be used for the next step.

Step c)

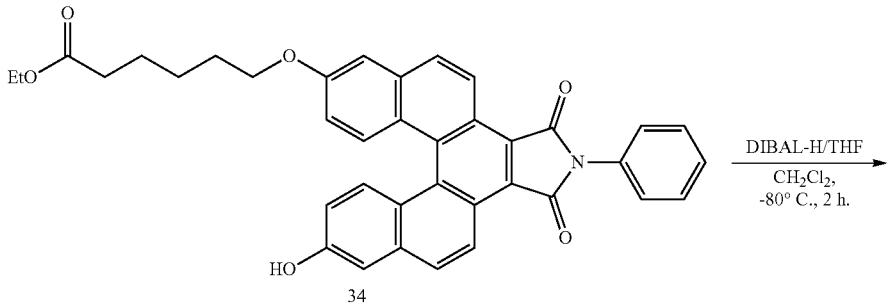

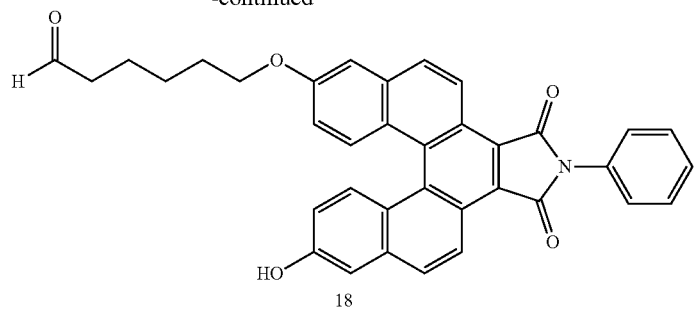

18

The compound 34 (0.12 g, 0.20 mmol) was dissolved in CH$_2$Cl$_2$ (45 mL) and stirred at −80° C. under argon atmosphere for 15 minutes. Then 1M DIBAL in THF (2.5 mL) was added dropwise. The reaction was stirred at −80° C. under argon atmosphere for 2 hours. The reaction was added methanol (15 mL) and water (15 mL) and stirred under argon atmosphere for 30 minutes. The solvent, then, was removed under reduced pressure. The crude product was purified by column chromatography (SiO$_2$, 15% to 50% EtOAc:Hexane) to give 6-((12-hydroxy-1,3-dioxo-2-phenyl-1H-dinaphtho[2,1-e:1',2'-g]isoindol-7-yl)oxy)hexanal or compound 18 as an orange solid (25 mg, 23% yield).

$^1$H NMR (500 MHz, DMSO-d$_6$): δ 9.80 (s, 1H), 9.07 (s, 1H), 8.31 (d, J=8.0 Hz, 2H), 8.08 (s, 2H), 7.95-7.97 (m, 2H), 7.52 (s, 4H), 7.41 (s, 1H), 6.87 (d, J=8.0 Hz, 2H), 4.25 (t, J=5.5 Hz, 2H), 2.51 (t, J=7.0 Hz, 2H), 1.59 (quin, J=7.5, 2H), 1.25 (quin, J=7.5 Hz, 2H), 0.89 (quin, J=7.5 Hz, 2H) ppm.

$^{13}$C NMR (125 MHz, DMSO-d$_6$): δ 173.40, 172.75, 167.80, 166.00, 140.15, 135.19, 134.23, 131.34, 130.88, 129.48, 129.09, 128.80, 127.87, 126.89, 122.33, 116.64, 115.93, 110.57, 107.79, 67.77, 77.21, 38.90, 37.39, 31.92, 30.56, 29.71, 23.98, 22.69 ppm.

FT-IR (KBr): ν$_{max}$ 3212, 2922, 2851, 1758, 1695, 1617, 1501, 1392, 1359, 1268, 1236, 1150, 1115, 858, 827, 742 cm$^{-1}$.

The Use of the Organic Compounds in the Present Invention as Molecular Reporter by Conjugating with Biomolecule After obtaining organic compounds as molecular reporters, the ability to conjugate the said compounds with biomolecules such as antibody or protein was investigated. The conjugation process depends on the binding groups on the said organic compounds. The molecular reporters in the present invention compose of two types of binding groups, i.e., carboxyl and aldehyde. The conjugated biomolecules were tested under ultraviolet irradiation. The conjugating ability testing are showed in the following examples.

EXAMPLE 19

The Testing of Ability to Conjugate a Molecular Reporter Containing Carboxyl Group to Biomolecule, in this Case an Antibody is Used as a Biomolecule Representative.

The conjugation between molecular reporter and antibody, in order to obtain antibody containing molecular reporter could be tested by immobilization of antibody or protein that could bind to antibody containing molecular reporter on a nitrocellulose membrane. The antibody containing molecular reporter could be captured by the immobilized antibody or protein on the membrane. The detection system is illustrated in FIG. 1.

The method of conjugation of synthesized molecular reporter containing carboxyl group which is used as a crosslinking group in the present invention consists of the following steps.

a) Prepare 10 mg/mL of molecular reporter (compound 6) in dimethyl sulfoxide (DMSO).

b) Prepare 10 mg/mL of 1-Ethyl-3-[3-dimethylaminopropyl] carbodiimide hydrochloride (EDC) in buffer solution containing 25 mM of 2-(N-morpholino)ethanesulfonic acid (MES buffer) pH 5.0.

c) Prepare 10 mg/mL of sulfo-N-hydroxysulfosuccinimide (sulfo-NHS) solution in buffer solution containing 25 mM of 2-(N-morpholino)ethanesulfonic acid (MES buffer), pH 5.0.

d) Prepare 1 mg/mL of antibody in phosphate-buffered saline (PBS) solution containing 1 mM potassium dihydrogen phosphate (KH$_2$PO$_4$), 154 mM sodium chloride, and 3 mM disodium hydrogen phosphate (Na$_2$HPO$_4$), pH 7.2.

e) Combine the solution with 10 μL each of step 1, 2 and 3, and incubate at room temperature for 15 minutes.

f) Combine the solution in step 5 with 50 μL of step 4, and incubate at room temperature for 2 hours.

g) Prepare protein solution to prevent non-specific binding by preparation 1% (w/v) of bovine serum albumin (BSA) in PBS solution.

h) Combine the solution in step 6 with 10 μL of step 7, and incubate at room temperature for 1 hour.

i) Keep a mixture solution at 4° C. until use.

After conjugation of molecular reporter and mouse antibody, the signal of molecular reporter and binding reactivity of antibody are tested. In order to apply this molecular reporter conjugated antibody in diagnostic, it may be tested by using membrane and 96-well plates.

EXAMPLE 20

The Testing of Ability to Conjugate Molecular Reporter Containing Aldehyde Group to Biomolecules, in this Case an Antibody is Used as an Example Biomolecule The conjugation between molecular reporter and antibody, in order to obtain antibody containing molecular reporter could be tested by immobilization of antibody or protein that could bind to antibody containing molecular reporter on a nitrocellulose membrane. The antibody containing molecular reporter could be captured by the immobilized antibody or protein on the membrane. The detection system is illustrated in FIG. 1.

The method of conjugation of the synthesized molecular reporter containing aldehyde group which was used as a crosslinking group in the present invention consists of the following steps.

a) Prepare 5 mg/mL of molecular reporter (compound 8 and 14) in dimethyl sulfoxide (DMSO).
b) Prepare 1 mg/mL of biomolecule in phosphate-buffered saline (PBS) solution containing 1 mM potassium dihydrogen phosphate ($KH_2PO_4$), 154 mM sodium chloride, and 3 mM disodium hydrogen phosphate ($Na_2HPO_4$), pH 7.2, in this case, the mouse antibody is used as an example.
c) Prepare 5M of sodium cyanoborohydride in 1M of sodium hydroxide (NaOH) solution.
d) Prepare blocking solution by preparation of 3M ethanolamine in phosphate-buffered saline, pH 6.6.
e) Combine the solution with 10 μL of step 1, 100 μL of step 2, and 1.1 μL of step 3, and incubate at room temperature for 2 hours.
f) Combine the solution in step 5 with 2.4 μL of step 4, and incubate at room temperature for 15 minutes.
g) Centrifuge solution from step 6 by centrifuge machine at 10,000 round per minute for 5 minutes.
h) Supernatant was collected and kept at 4° C. until use.

After conjugation of molecular reporter and mouse antibody, the signal of molecular reporter and binding reactivity of antibody are tested. In order to apply this molecular reporter conjugated antibody in diagnostic, it may be tested by using membrane and 96-well plate.

EXAMPLE 21

Figure 2:
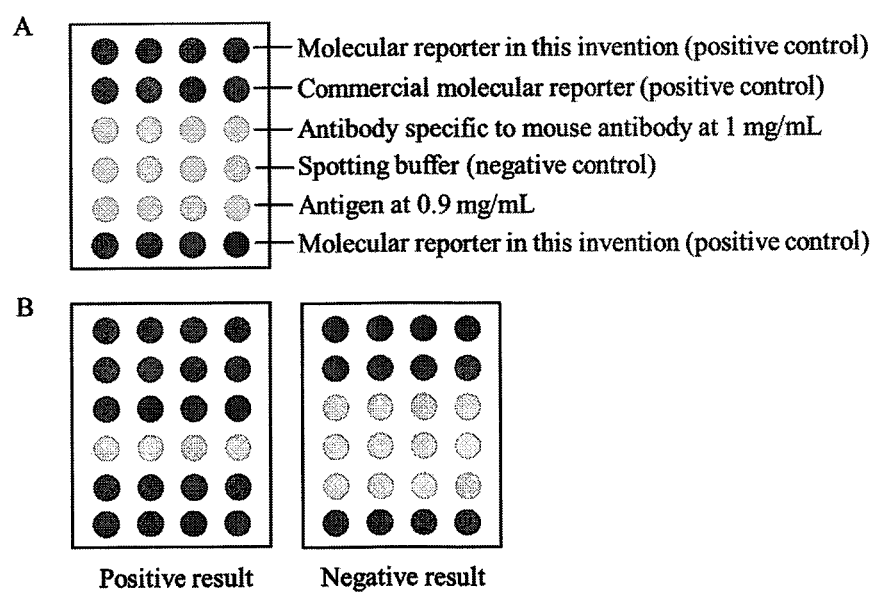
FIG. 2. Schematic of antibody spots on membrane (A), and the results interpretation (B).

The Testing of Conjugation of Molecular Reporter in this Invention to Antibody on Membrane Method of testing of conjugation molecular reporter in this invention to antibody on membrane consists of the following steps a) Prepare spotting of 1 mg/mL antibody that could capture the molecular reporter conjugated antibody (FIG. 1A), and 0.90 and 0.45 mg/mL of antigen that molecular reporter conjugated antibody could bind (FIG. 1B) in carbonate buffer solution containing 50 mM carbonate and 50% v/v glycerol, pH 9.6. Both of antibody and antigen are spotted on nitrocellulose membrane using an automatic microarrayer machine.
b) Keep the membranes from step 1 at 4° C. for 12-16 hours.
c) Block non-specific binding with 2% (w/v) skimmed milk in PBS containing 0.05% Tween (PBST), and incubate at room temperature for 1 hour.
d) Wash the membranes from step 3 with 400 μL of PBST per membrane for three times
e) Add 18 μg/mL of antibody conjugating with molecular reporter (compound 6, 8, and 14) for each membrane, and incubate at room temperature for 1 hour
f) Wash the membranes from step 5 with 400 μL/membrane of PBST for three times Each spot on nitrocellulose membranes is illustrated in FIG. 2A, and the interpreting results are shown in FIG. 2B.

The membranes from step 6 were observed under ultraviolet light 250-450 nm. The results gave high signal when observed at 312 nm for compound 6, and 8, whereas compound 14 showed high signals at 365 nm.

Figure 3:
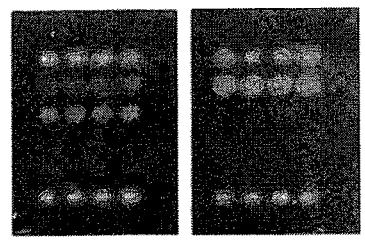
FIG. 3. Testing of the molecular reporters in the present invention conjugated mouse antibody on membrane.
Figure 3:
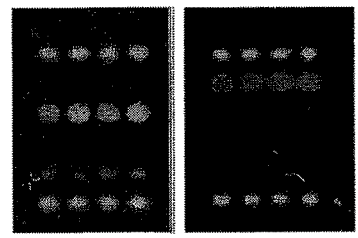
Figure 3:
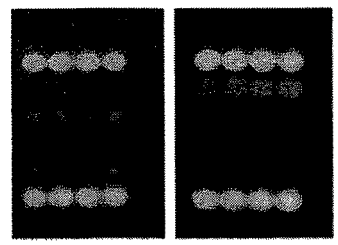

The results of antibody conjugating molecular reporter by membrane method were shown in FIG. 3, where A) was compound 6, B) was compound 8, and C) was compound 14. The spots of antibody capturing mouse antibody and antigen showed signals (Left), whereas the membranes adding buffer without molecular conjugated antibody showed negative results (Right)

EXAMPLE 22

The Testing of Binding Reactivity of Antibody After Conjugated with Molecular Reporter on 96-Well Plates The binding reactivity of antibody conjugating molecular reporter (compound 6, compound 8, and compound 14) to antigen could be tested with an immobilization of antigen on wells of 96-well plates. The molecular reporter conjugated antibody was added into the wells. The antibody would bind to the antigen coating wells. Horseradish peroxidase labeled antibody specific to mouse antibody was used as a reporter molecule for reporting binding reactivity. The results of molecular reporter conjugated antibody were compared with results of antibody without molecular reporter conjugation.

The method for testing binding reactivity of molecular reporter conjugated antibody and antigen in 96-well plate consists of the following steps.

a) Prepare 2 μg/mL of antigen in carbonate buffer containing 50 mM carbonate, pH 9.6, and immobilize antigen (100 μL/well) in 96-well plate.
b) Incubate 96-well plate in step 1 at 4° C. for 12-16 hours.
c) Block non-specific binding with 300 μL/well of 2% bovine serum albumin in phosphate-buffered saline containing 0.05% Tween (PBST), and incubate at room temperature for 1 hour.
d) Wash 96-well plates in step 3 with 300 μL/well of PBST for 3 times.
e) Add 100 μL/ well of 2 μg/mL of antibody conjugating molecular reporter (compound 6, compound 8, and compound 14), and incubate at room temperature for 1 hour.
f) Wash 96-well plates in step 5 with 300 μL/well of PBST for 3 times.
g) Add 100 μL/well of horseradish peroxidase labeled antibody specific to mouse antibody (dilution at 1:10,000), and incubate at room temperature for 1 hour.
h) Wash 96-well plates in step 7 with 300 μL/well of PBST for 3 times.
i) Add 100 μL/well of substrate solution for horseradish peroxidase which is 3,3',5,5'-Tetramethylbenzidine, and incubate at room temperature for 30 minutes.
j) Add 50 μL/well of sulfuric acid ($H_2SO_4$) for stop reaction.
k) Measure signals at 450 nm.

Figure 4:
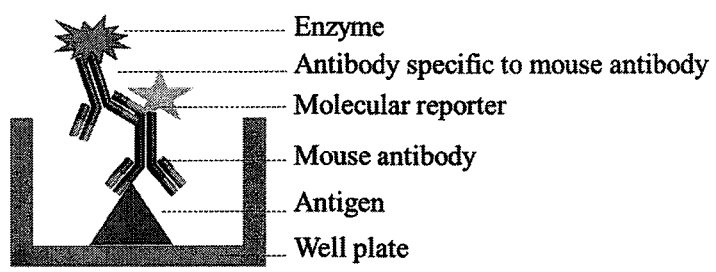
FIG. 4. Schematic of testing of binding reactivity between molecular reporter the present invention conjugated antibody and antigen.
Figure 5:
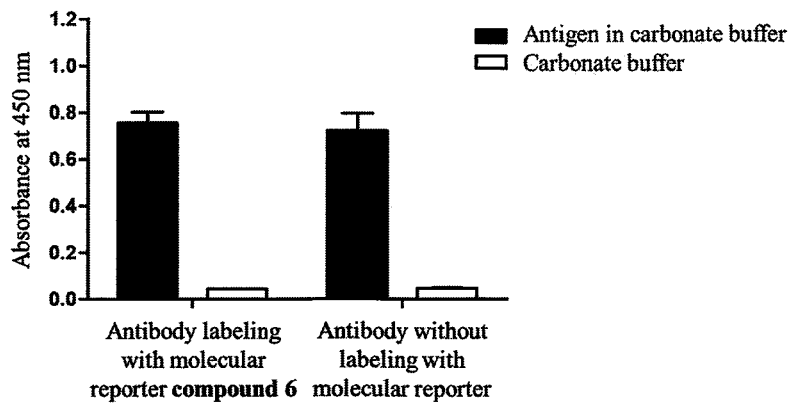
FIG. 5. Binding reactivity of antibody conjugated with and without molecular reporter in the present invention.
Figure 5:
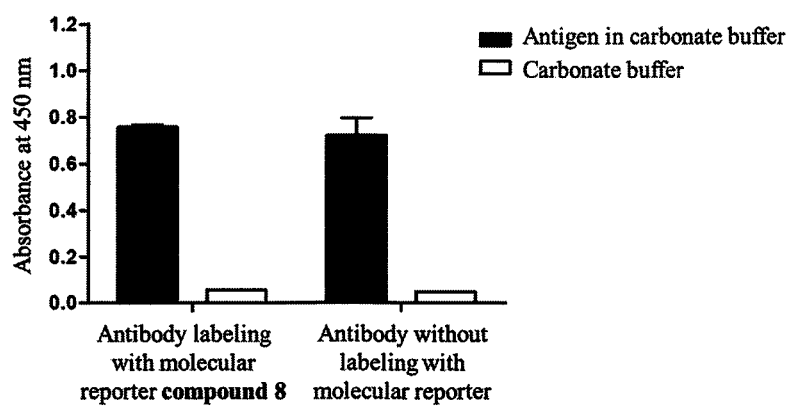
Figure 5:
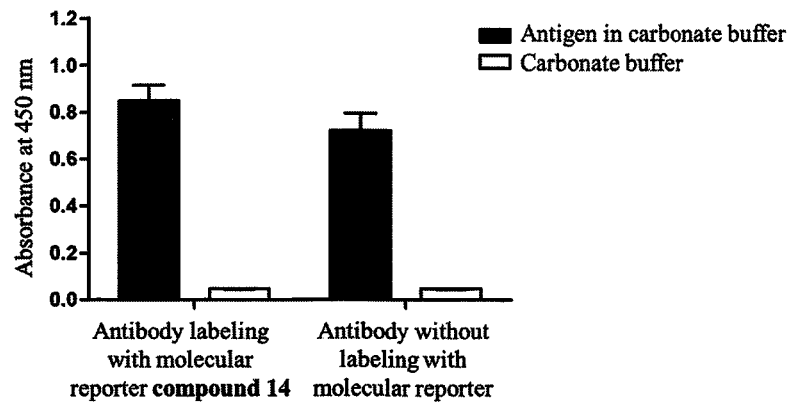

The detection system of binding reactivity between antibody conjugating molecular reporter (compound 6, compound 8, and compound 14) and antigen is illustrated in FIG. 4. The results of antibody conjugating molecular reporter (compound 6, compound 8, and compound 14) showed that antibody could bind to antigen. The molecular reporters did not affect the binding reactivity of antibody when were compared with antibody without any conjugation. The results showed in FIG. 5, where (A) was compound 6, (B) was compound 8, and (C) was compound 14.

What is claimed is:
1. A helicene derivative compound represented by the following chemical formula (1)

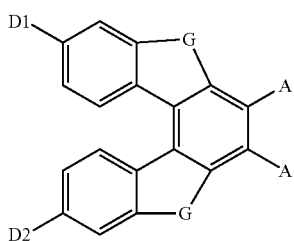

(1)

wherein:

G is a connecting group comprising 2 carbon atoms selected from the group consisting of Ethane

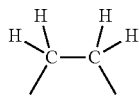

and

Ethylene

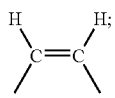

A is a separated or connected group selected from the group consisting of

Cyano
 —CN and
Imide

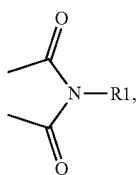

wherein R1 is selected from the group consisting of

Phenyl

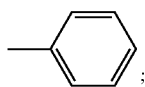

Alkyl

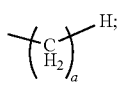

when a is a number of carbon atoms in aliphatic hydrocarbon and a ranges from 1 to 7; and Alkanoic acid

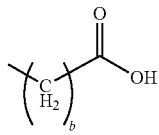

when b is a number of carbon atoms in aliphatic hydrocarbon and b ranges from 1 to 7;

D1 is selected from the group consisting of

Oxyalkanoic acid

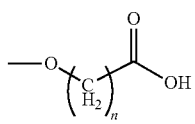

when n is a number of carbon atoms in aliphatic hydrocarbon and n ranges from 1 to 7;

Oxyalkanal

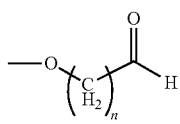

when n is a number of carbon atoms in aliphatic hydrocarbon and n ranges from 1 to 7; and Oxyalkanesulfonate

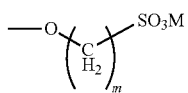

when M is a metal atom selected from the group consisting of sodium and potassium,
m is a number of carbon atoms in aliphatic hydrocarbon and m ranges from 3 or 4;

D2 is selected from the group consisting of

Hydroxy
 —OH

Oxyalkanoic acid

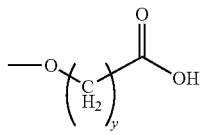

when y is a number of carbon atoms in aliphatic hydrocarbon and y ranges from 1 to 7;

Oxyalkanal

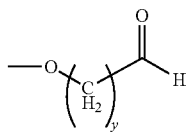

when y is a number of carbon atoms in aliphatic hydrocarbon and y ranges from 1 to 7;
Alkyl oxyalkanoate

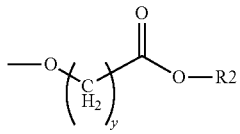

(5)

when y is a number of carbon atoms in aliphatic hydrocarbon and y ranges from 1 to 7,
R2 is selected from the group consisting of methyl and ethyl group;
Oxyalkanol

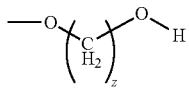

(20)

when z is a number of carbon atoms in aliphatic hydrocarbon and z ranges from 2 to 8; and
Oxyalkanesulfonate

(30)

when M is a metal atom selected from the group consisting of sodium and potassium,
m is a number of carbon atoms in aliphatic hydrocarbon and m ranges from 3 or 4.

2. The [5]helicene derivative compound according to claim 1, wherein
a) A is cyano; G is ethane; D1 is oxyalkanoic acid; and D2 is selected from the group consisting of hydroxy, oxyalkanoic acid, and oxyalkanesulfonate;
b) A is cyano; G is ethane; D1 is oxyalkanal; and D2 is selected from the group consisting of hydroxy, alkyl oxyalkanoate, oxyalkanal, and oxyalkanol;
c) A is cyano; G is ethylene; D1 is oxyalkanoic acid; and D2 is selected from the group consisting of hydroxy, oxyalkanoic acid, and oxyalkanesulfonate;
d) A is cyano; G is ethylene; D1 is oxyalkanal; and D2 is selected from the group consisting of hydroxy, and oxyalkanol;
e) A is imide wherein R1 is selected from the group consisting of phenyl and alkyl; G is selected from the group consisting of ethane and ethylene; D1 is oxyalkanal; and D2 is selected from the group consisting of hydroxy, oxyalkanal, alkyl oxyalkanoate, oxyalkanol, and oxyalkanesulfonate; and
f) A is imide wherein R1 is alkanoic acid; G is ethane; D1 and D2 are oxyalkanesulfonate.

3. The [5]helicene derivative compound according to claim 1, wherein the alkyl chain of the imide group is straight chain, and the alkanoic acid of the imide group is straight chain.

4. A method of preparing a [5]helicene derivative compound, comprising the steps of:
a) an O-alkylation reaction of the [5]helicene compound in formula (4), selected from the [5]helicene compound in formula (4) wherein A1 is an imide or a cyano, with an haloalkanoic acid alkyl ester (I) with a first base in a first organic solvent to give [5]helicene compound (5) and/or compound (6) as an intermediate molecule;

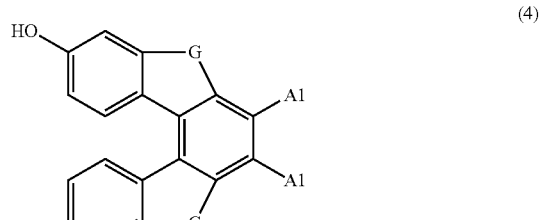

(4)

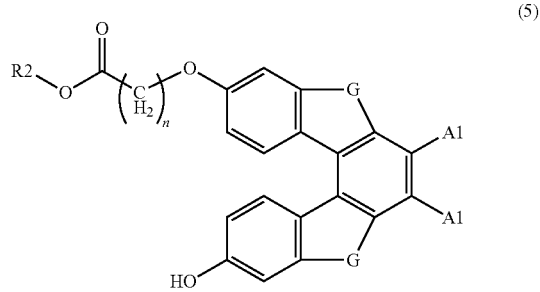

(5)

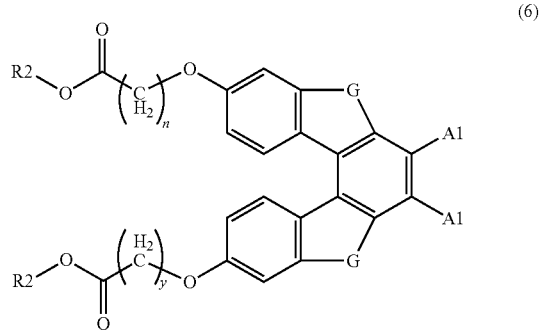

(6)

wherein the haloalkanoic acid alkyl ester (I) has a chemical formula:

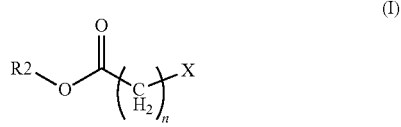

(I)

wherein n is a number of carbon atoms of aliphatic hydrocarbon in the haloalkanoic acid alkyl ester (I) where n ranges from 1 to 7; wherein the first base is selected from the group consisting of sodium bicarbonate ($NaHCO_3$), potassium bicarbonate ($KHCO_3$), sodium carbonate ($Na_2CO_3$), and potassium carbonate ($K_2CO_3$), wherein the first organic solvent is selected from the group consisting of dimethyl formamide, acetone, acetonitrile, and a mixture thereof;
b) a hydrolysis reaction of the [5]helicene compound (5) or compound (6) with a second base in a second organic solvent at a temperature in the range of 25-150° C. for 1-24 hours, followed by an acid treatment with an acid at a pH of 0 to obtain [5]helicene compound (7) or compound (8) as a final product or an intermediate;

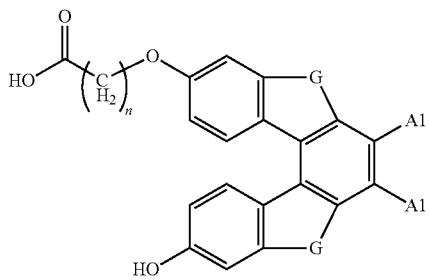

(7)

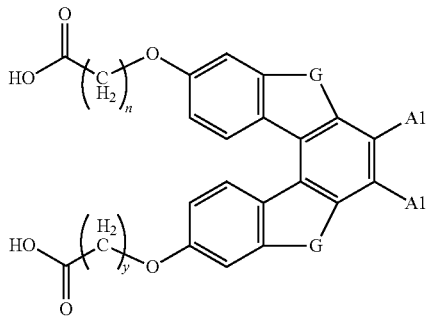

(8)

wherein the second base is selected from the group consisting of sodium hydroxide (NaOH), potassium hydroxide (KOH), and lithium hydroxide (LiOH), wherein the organic solvent 2 is selected from the group consisting of ethanol, methanol, tetrahydrofuran, dioxane, dichloromethane, and a mixture thereof, and wherein the acid is selected from the group consisting of hydrochloric acid, and sulfuric acid;

c) an O-alkylation reaction of the intermediate compound containing an OH group, selected from [5]helicene compounds (4), (5) or (7), with an alkane sultone (II) and a third base in a third organic solvent to obtain [5]helicene compound (9), compound (10) or compound (11) as final product of intermediate;

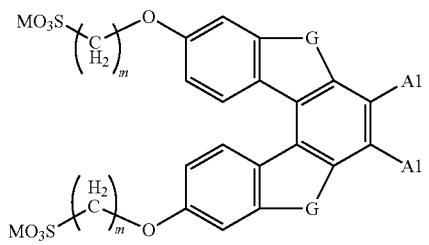

(9)

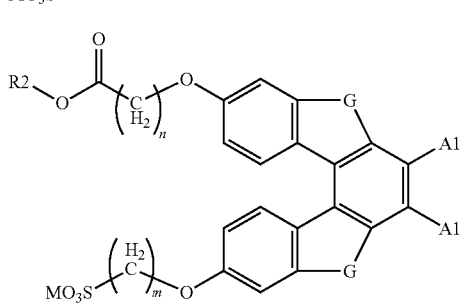

(10)

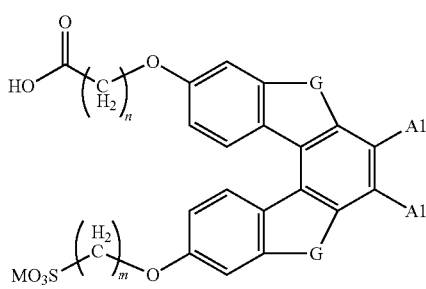

(11)

wherein the alkane sultone (II) is a straight chain and has a chemical formula:

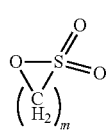

(II)

wherein m is a number of carbon atoms in aliphatic hydrocarbon and equals 3 or 4;

wherein the third base is selected from the group consisting of sodium hydroxide (NaOH), potassium hydroxide (KOH), sodium methoxide (NaOMe), potassium methoxide (KOMe), sodium ethoxide (NaOEt), and potassium ethoxide (KaOEt), wherein the third organic solvent is selected from the group consisting of methanol, ethanol, acetone, and acetonitrile; and d) a reduction reaction of the intermediate containing ester group, selected from [5]helicene compounds (5), (6), or (10), using diisobutylaluminum hydride, (DIBAL-H) in a fourth organic solvent to obtain a [5]helicene compound (12), compound (13) and/or compound (14) and/or compound (15), or compound (16) as a final product

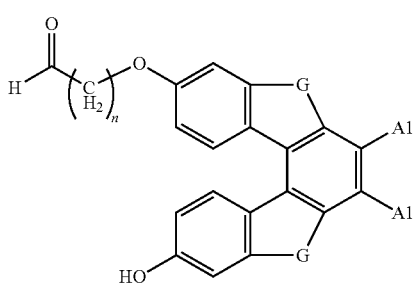

(12)

-continued

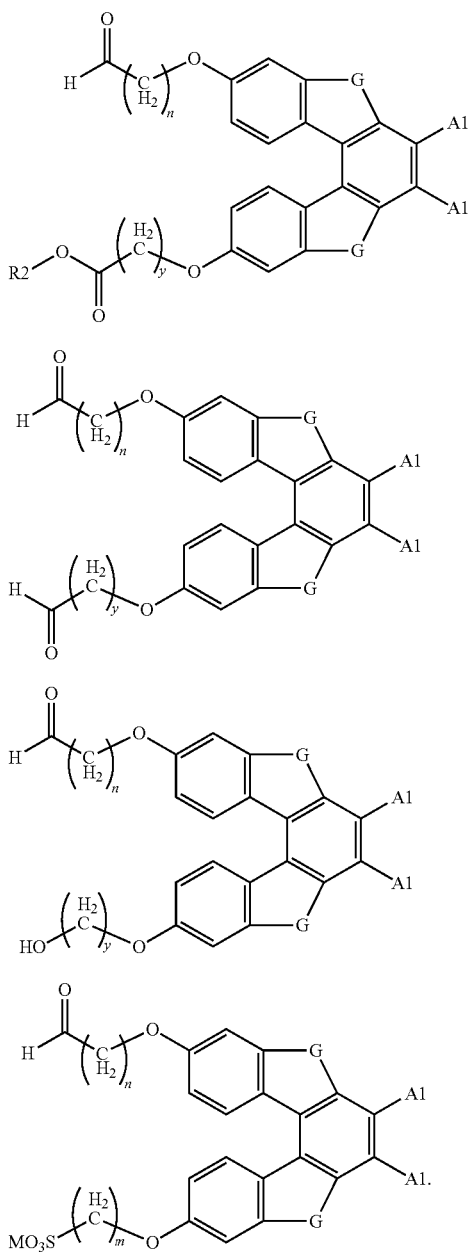

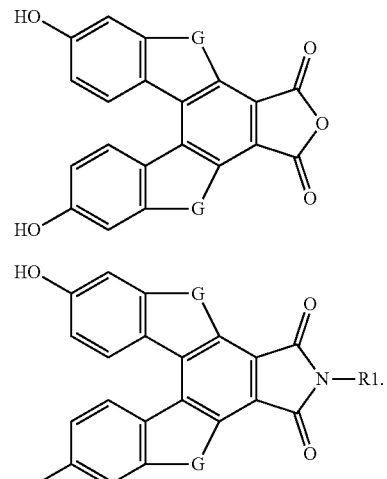

wherein the fourth organic solvent is selected from the group consisting of dichloromethane, tetrahydrofuran, toluene, and a mixture thereof.

5. The method according to claim 4, wherein the O-alkylation reaction in step a) is carried out at a temperature in a range of 60-160° C. for 2-12 hours.

6. The method according to claim 4, wherein the O-alkylation reaction in step c) is carried out at a temperature in a range of 25-80° C. for 6-120 hours.

7. The method according to claim 4, wherein the reduction reaction in step d) is carried out at a temperature in a range of −90° C. to room temperature for 1-4 hours.

8. The method according to claim 4, wherein the O-alkylation reaction in step a) further comprises an imidation reaction between a [5]helicene compound in the formula (2), a primary amine (III), and a second acid in a fifth organic solvent to obtain a [5]helicene isoindole dione compound in the formula (3)

wherein the second acid is selected from the group consisting of acetic acid, hydrochloric acid, and sulfuric acid, wherein the fifth organic solvent is selected from the group consisting of dimethyl formamide, dimethyl sulfoxide, acetonitrile, toluene, benzene, and a mixture thereof, wherein the primary amine (III) has a chemical formula:

$$H_2N-R1 \quad (III)$$

wherein:
R1 is selected from the group consisting of
Phenyl

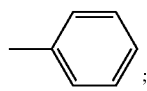

Alkyl

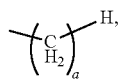

when a is a number of carbon atoms in straight chain aliphatic hydrocarbon, and a ranges from 1 to 7; and
Alkanoic acid

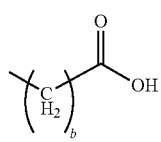

when b is a number of carbon atoms in straight chain aliphatic hydrocarbon, and b ranges from to 1 to 7.

9. The method according to claim 8, wherein the imidation reaction is carried out at a temperature in a range of 80-160° C. for 2-12 hours.

10. A method for sensing at least one microbial, toxin, or toxicant in a sample comprising:
   (i) contacting the sample with a [5]helicene derivative compound according to claim 1 and;
   (ii) crosslinking a biomolecule selected from the group consisting of a protein, antibody, and peptide as a molecular reporter to sense the microbial, toxin, or toxicant by photoluminescence spectroscopy.

* * * * *

UNITED STATES PATENT AND TRADEMARK OFFICE
CERTIFICATE OF CORRECTION

| | |
|---|---|
| PATENT NO. | : 11,578,040 B2 |
| APPLICATION NO. | : 16/338031 |
| DATED | : February 14, 2023 |
| INVENTOR(S) | : Thanasat Sooksimuang et al. |

It is certified that error appears in the above-identified patent and that said Letters Patent is hereby corrected as shown below:

On the Title Page

Item (57), Line 15 of ABSTRACT, "it-conjugating system" should read --π-conjugating system--.

In the Claims

Claim 1, Column 70, Line 66, "A helicene derivative compound" should read --A [5]helicene derivative compound--.

Claim 5, Column 77, Line 56, "ata" should read --at a--.

Claim 7, Column 77, Line 62, "ata" should read --at a--.

Claim 9, Column 78, Line 66, "ata" should read --at a--.

Signed and Sealed this
Sixth Day of June, 2023

Katherine Kelly Vidal
*Director of the United States Patent and Trademark Office*